(12) United States Patent
Bornzin et al.

(10) Patent No.: US 7,848,809 B1
(45) Date of Patent: Dec. 7, 2010

(54) PAC THERAPY

(75) Inventors: Gene A. Bornzin, Simi Valley, CA (US); Peter Boileau, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 347 days.

(21) Appl. No.: 11/735,860

(22) Filed: Apr. 16, 2007

Related U.S. Application Data

(63) Continuation of application No. 11/349,497, filed on Feb. 6, 2006.

(51) Int. Cl.
*A61N 1/08* (2006.01)
(52) U.S. Cl. .......................................... 607/9
(58) Field of Classification Search ............... 607/9, 607/14
See application file for complete search history.

(56) References Cited

U.S. PATENT DOCUMENTS

| | | | | |
|---|---|---|---|---|
| 5,313,953 | A * | 5/1994 | Yomtov et al. | 607/36 |
| 5,507,783 | A * | 4/1996 | Buchanan | 607/14 |
| 5,643,326 | A | 7/1997 | Weiner et al. | |
| 5,683,429 | A * | 11/1997 | Mehra | 607/14 |
| 5,772,691 | A * | 6/1998 | Routh et al. | 607/9 |
| 5,978,709 | A | 11/1999 | Begemann et al. | |
| 6,185,459 | B1 * | 2/2001 | Mehra et al. | 607/14 |
| 6,243,606 | B1 | 6/2001 | Mann et al. | |
| 7,181,277 | B1 * | 2/2007 | Shelchuk et al. | 607/9 |
| 7,593,773 | B2 * | 9/2009 | Boute et al. | 607/9 |
| 2004/0215273 | A1 * | 10/2004 | Van Bolhuis et al. | 607/27 |
| 2006/0167513 | A1 * | 7/2006 | Rouw et al. | 607/17 |

FOREIGN PATENT DOCUMENTS

EP 0965361 A2 12/1999

OTHER PUBLICATIONS

Capucci, Alessandro et al., "Atrial premature beats coupling interval determines lone paroxysmal atrial fibrillation onset," Int J Cardiol 1992;36:87-93.
Mehra, Rahul et al., "Prevention of Atrial Fibrillation/Flutter by Pacing Techniques," (from Saksena S, Luderitz B (eds.) Intervention Electrophysiology: A Textbook, Second Edition, 1996;34:521-540.
NonFinal Office Action, mailed Apr. 16, 2009—Related U.S. Appl. No. 11/349,497.
NonFinal Office Action, mailed Jun. 22, 2009—Related U.S. Appl. No. 11/735,872.
NonFinal Office Action, mailed Nov. 19, 2009: Related U.S. Appl. No. 11/349,497.
NonFinal OA (Restriction), mailed Dec. 9, 2009: Related U.S. Appl. No. 11/735,872.
Final Office Action, mailed May 26, 2010: Related U.S. Appl. No. 11/349,497.
Final Office Action, mailed May 13, 2010: Related U.S. Appl. No. 11/735,872.

* cited by examiner

*Primary Examiner*—Scott M Getzow
*Assistant Examiner*—Joseph M Dietrich

(57) ABSTRACT

An implantable cardiac device is programmed to detect and classify premature atrial contractions (PACs). In the described implementation, the device uses timing based techniques to distinguish PACs from native sinus P-waves. The device is also able to detect and count a salvo of consecutive PACs for diagnostic purposes.

20 Claims, 19 Drawing Sheets

PAC THERAPY

CROSS REFERENCE TO RELATED APPLICATIONS

This application is a continuation of copending U.S. patent application Ser. No. 11/349,497, filed Feb. 6, 2006, titled "PAC Therapy."

FIELD OF THE INVENTION

Subject matter disclosed herein generally relates to implantable cardiac devices and methods, and particularly, devices and methods to detect premature atrial contractions and apply responsive pacing therapy.

BACKGROUND OF THE INVENTION

A premature atrial contraction (PAC) is a native depolarization arising in the atrium that is premature with respect to the basic sinus cycle. Also called atrial premature beats or atrial premature contractions, premature atrial contractions occur when a site in the atria other than the sinus node develops automaticity of a rate greater than that of the sinus node. This site from which the contraction originates is called an ectopic focus. An ectopic focus can usurp control of the atria from the sinus node for one or a few consecutive beats causing a single PAC or a "salvo" of consecutive PACs. If the ectopic focus remains in control for a long period, the heart condition is referred to as a focal atrial tachycardia.

PACs can differ from sinus-initiated atrial contractions in many respects, including in their timing, in the duration of their action potential and effective refractory period, and in their speed and direction of propagation through the atria. The action potential duration and effective refractory period of atrial myocytes shortens as the rate at which they are activated increases. Therefore, if a PAC occurs very soon after a previous atrial contraction, effective refractory periods around the atria can be significantly shorter for the PAC than they were for the previous contraction. The relationship between the effective refractory period and the previous interval duration may not be uniform throughout the atria. Therefore a PAC can cause dispersion of refractory periods. This means portions of the atria become excitable before other portions, maybe while a wave of excitation is still present. This condition sets the stage for reentrant arrhythmia.

PACs are often associated with the onset of atrial flutter and atrial fibrillation. A single PAC or a salvo of PACs can trigger atrial fibrillation or other reentrant atrial tachycardias. Additionally, the frequency at which PACs occur can be an indicator of susceptibility of the atria to atrial fibrillation or atrial tachycardias. PACs may also trigger arrhythmias by occurring at a moment when the atrium in not uniformly recovered from the previous beat.

Typically pacemakers do not recognize PACs as such. A PAC will either occur during an atrial refractory period and be ignored completely, or it will occur during an atrial alert period and be treated as a sinus P-wave. A pacemaker in DDD mode may track a PAC and thereby cause an irregularity in the ventricular rhythm. A pacemaker in DDI mode may be inhibited by a PAC, disrupting AV synchrony and setting the stage for a retrograde P-wave. There is a need for improved techniques for accurately detecting PACs and where appropriate, administering responsive pacing therapy.

SUMMARY

An implantable cardiac device is programmed to detect and classify premature atrial contractions (PACs). In the described implementation, the device uses timing-based techniques to distinguish PACs from P-waves. The device is also able to detect and count a salvo of consecutive PACs for diagnostic purposes.

Following detection and classification of a PAC, the implantable cardiac device can be operated in a mode to administer responsive pacing therapy. In the described implementation, the responsive pacing therapy is in the form of an atrial extrastimulus, which is intended to preempt initiation of a reentrant tachycardia. The atrial extrastimulus is timed to occur late enough after a PAC to ensure atrial capture of the extrastimulus, but early enough that the resulting atrial depolarization does not conduct through the AV node to the ventricles if the PAC has already done so. If both of these criteria cannot be met, the implantable cardiac device may be configured to inhibit the atrial extrastimulus.

The implantable cardiac device can also be configured to reduce any disruption to other pacing therapies that might be caused by the atrial extrastimulus. For example, for a patient with AV block, the device may avoid pacing the ventricle if too much time has elapsed since the last atrial depolarization in order to prevent initiating pacemaker-mediated tachycardia (PMT). Also, the implantable cardiac device may optionally adjust the atrial pacing rate following the PAC and responsive atrial extrastimulus to avoid a short-long cycle length sequence and provide a smooth transition to the base rate over one or more pacing cycles.

BRIEF DESCRIPTION OF THE DRAWINGS

Features and advantages of the described implementations can be more readily understood by reference to the following description taken in conjunction with the accompanying drawings. In the description that follows, like numerals or reference designators will be used to reference like parts or elements throughout.

FIG. 11 shows a PAC occurring early in a cycle, FIG. 12 shows a PAC occurring later in the cycle, and FIG. 13 shows a PAC occurring very late in the cycle. FIGS. 11-13 illustrate different pacing responses depending upon the position of the PAC within the cycle.

FIG. 15 illustrates one possible pacing response in this situation.

FIG. 16 illustrates one possible pacing response in this situation.

OVERVIEW

An implantable cardiac device is programmed to detect and classify premature atrial contractions (PACs) and then selectively administer responsive pacing therapy. The following discussion describes first an exemplary cardiac device and then a PAC mode of operation in which PACs are detected and responsive therapy is applied.

Exemplary Device

Figure 1:
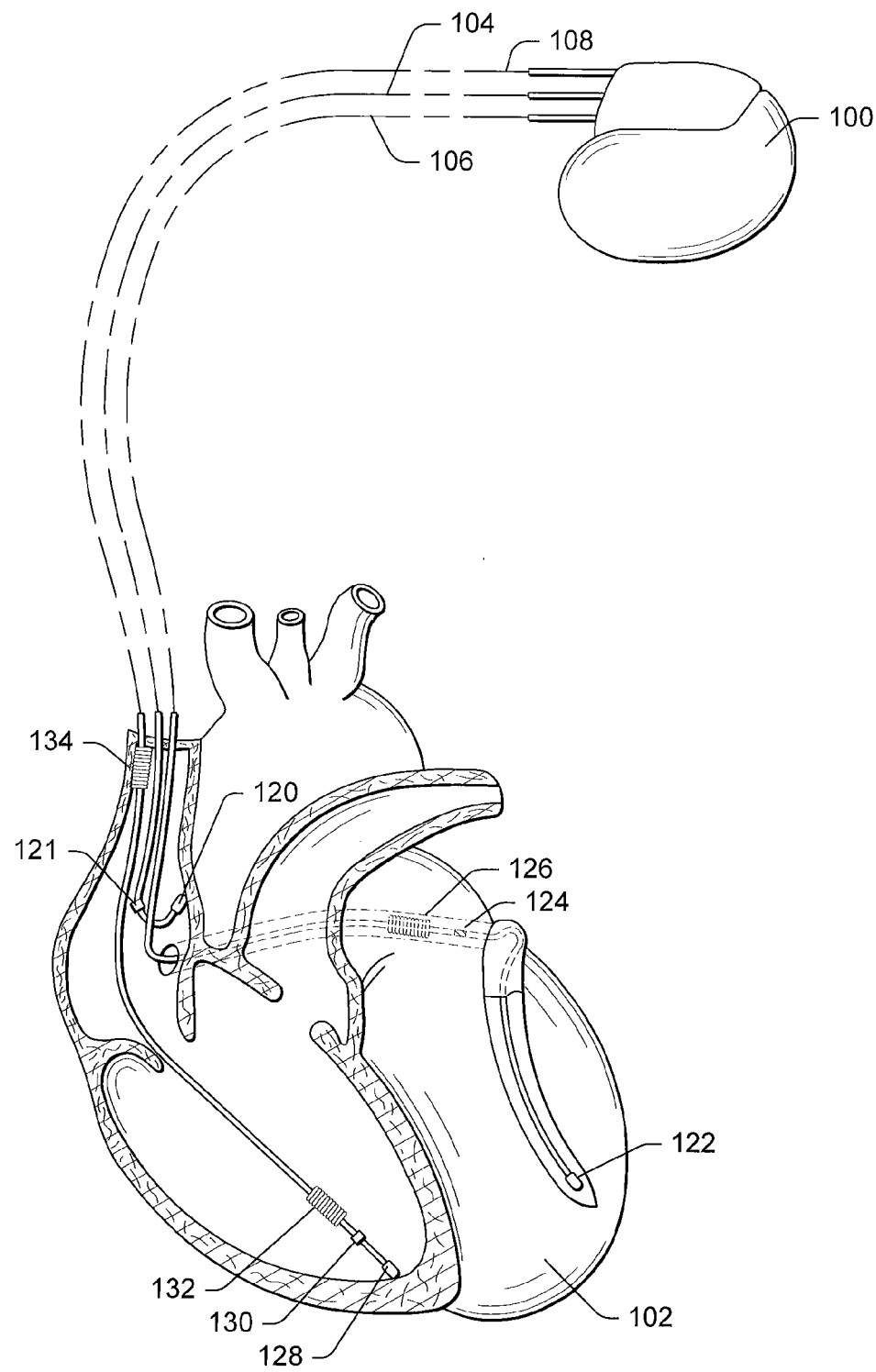
FIG. 1 is a simplified diagram illustrating an implantable cardiac device in electrical communication with at least three leads implanted into a patient's heart for multi-chamber sensing and delivering multi-chamber stimulation therapy.

FIG. 1 shows an exemplary implantable cardiac device 100 in electrical communication with a patient's heart 102 for monitoring heart activity and/or delivering stimulation therapy, such as pacing therapies. Three leads—a right atrial lead 104, a coronary sinus lead 106, and a right ventricular lead 108—interconnect the device 100 with the patient's heart 102 to support multi-chamber detection and stimulation therapy.

The right atrial lead 104 supports an atrial tip electrode 120, which typically is implanted in the patient's right atrial appendage and optionally a ring electrode 121. The right atrial lead 104 enables the device to sense atrial cardiac signals and apply pacing therapy to the right atrial chamber.

The coronary sinus lead 106 positions a left ventricular tip electrode 122 adjacent to the left ventricle and/or additional electrode(s) adjacent to the left atrium, such as a left atrial ring electrode 124 and a left atrial coil electrode 126. The coronary sinus lead 106 enables the device 100 to sense left atrial and ventricular cardiac signals and administer left chamber pacing therapy. In the illustrated arrangement, the left ventricular tip electrode 122 is used to sense atrial and ventricular cardiac signals and deliver left ventricular pacing therapy. The left atrial ring electrode 124 is employed for applying left atrial pacing therapy, and the left atrial coil electrode 126 is used for shocking therapy.

The right ventricular lead 108 is electrically coupled to a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of receiving cardiac signals, and delivering stimulation in the form of pacing and shock therapy to the right ventricle.

Figure 2:
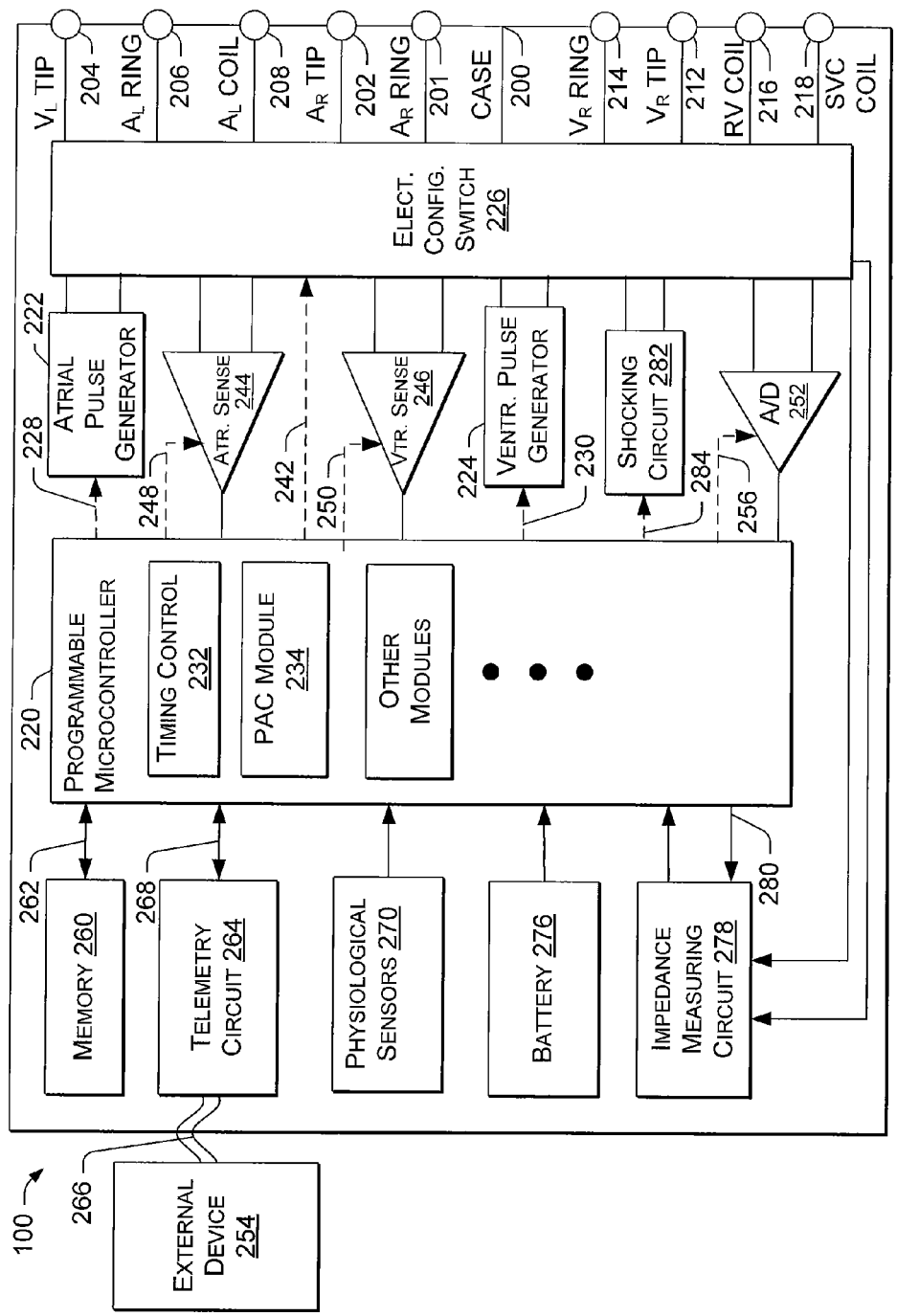
FIG. 2 is a simplified functional block diagram of the multi-chamber implantable cardiac device.

FIG. 2 shows exemplary components of the implantable cardiac device 100. The components are housed in housing 200, which is often referred to as the "can", "case", "encasing", or "case electrode". The housing 200 may be programmably selected to act as the return electrode for unipolar modes or it may be used as a return electrode alone or in combination with one or more of the coil electrodes 126, 132 and 134 for shocking purposes. The housing 200 further includes a connector (not shown) having a plurality of terminals 202, 204, 206, 208, 212, 214, 216, and 218 (shown schematically and, for convenience, the names of the electrodes to which they are connected are shown next to the terminals), including:

a right atrial tip terminal (AR TIP) 202 for atrial tip electrode 120;

a right atrial ring terminal (AR RING) 201 for atrial ring electrode 121;

a left ventricular tip terminal (VL TIP) 204 for left ventricular tip electrode 122;

a left atrial ring terminal (AL RING) 206 for left atrial ring electrode 124;

a left atrial shocking terminal (AL COIL) 208 for left atrial coil electrode 126;

a right ventricular tip terminal (VR TIP) 212 for right ventricular tip electrode 128;

a right ventricular ring terminal (VR RING) 214 for right ventricular ring electrode 130;

a right ventricular shocking terminal (RV COIL) 216 for RV coil electrode 132; and an SVC shocking terminal (SVC COIL) 218 for SVC coil electrode 134.

The implantable cardiac device 100 includes a programmable microcontroller 220 that controls various operations of the ICTD, including cardiac monitoring and stimulation therapy. Microcontroller 220 includes a microprocessor (or equivalent control circuitry), RAM and/or ROM memory, logic and timing circuitry, state machine circuitry, and I/O circuitry. Examples of two possible state machines that may be implemented in the programmable microcontroller 220 to facilitate PAC detection and response are described below in more detail beneath the heading "Exemplary State Machines".

Device 100 further includes an atrial pulse generator 222 and a ventricular pulse generator 224 that generate pacing pulses for delivery by the right atrial lead 104, the coronary sinus lead 106, and/or the right ventricular lead 108 via an electrode configuration switch 226. The switch 226 includes multiple switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches.

To provide stimulation therapy in each of the four chambers of the heart, the atrial and ventricular pulse generators 222 and 224 may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 is illustrated as including timing control circuitry 232 to control the timing of the stimulation pulses (e.g., pacing rate, atrio-ventricular (AV) delay, atrial interconduction (AA) delay, or ventricular interconduction (VV) delay, etc.). The timing control circuitry 232 may also be used for the timing of refractory periods, blanking intervals, noise detection windows, evoked response windows, alert intervals, marker channel timing, and so on.

The microcontroller 220 is also equipped with a premature atrial contraction (PAC) module 234 to detect a single PAC or a salvo of consecutive PACs. The PAC module 234 utilizes timing-based techniques to distinguish PACs from native sinus-originating P-waves. Upon detection of a native P-wave, the PAC detector 234 initiates a detection window following a short delay. If another atrial contraction is detected during the window, the PAC module classifies the atrial contraction as a premature atrial contraction. The PAC module 234 may implement a counter to count the one or more PACs that might occur in succession. With detection of each atrial contraction, the PAC module 234 classifies the contraction as a premature atrial contraction, the counter is incremented, and the detection window is restarted following the short delay. This is repeated until the detection window times out without detection of an atrial contraction. Based on the PAC count, the PAC module 234 labels individual PACs to differentiate them in the salvo of PACs for diagnostic purposes.

The PAC module 234 may also provide for PAC therapy, for example, to administer pacing therapy applied to heart in response to detection of a PAC. In the described implementation, the responsive pacing therapy is in the form of an atrial extrastimulus, which is intended to preempt initiation of a reentrant tachycardia. The atrial extrastimulus is a one-time stimulation pulse that is timed to occur late enough after a PAC to ensure atrial capture, but early enough that the resulting atrial depolarization does not conduct through the AV node to the ventricles if the PAC has already done so. If both of these criteria cannot be met, the device may be configured to inhibit application of the atrial extrastimulus.

The components 232, 234 and various other components may be implemented in hardware as part of the microcontroller 220, or as software/firmware instructions programmed into the device and executed on the microcontroller 220 during certain modes of operation. Although not shown, the microcontroller 220 may further include other dedicated circuitry and/or firmware/software components that assist in monitoring various conditions of the patient's heart and managing pacing therapies.

Atrial sensing circuits 244 and ventricular sensing circuits 246 may also be selectively coupled to the right atrial lead 104, coronary sinus lead 106, and the right ventricular lead 108, through the switch 226 to detect the presence of cardiac activity in each of the four chambers of the heart. The sensing circuits 244 and 246 may include dedicated sense amplifiers, multiplexed amplifiers, or shared amplifiers. Switch 226 determines the "sensing polarity" of the cardiac signal by selectively closing the appropriate switches. In this way, the clinician may program the sensing polarity independent of the stimulation polarity.

Each sensing circuit 244 and 246 may employ one or more low power, precision amplifiers with programmable gain and/or automatic gain control, bandpass filtering, and a threshold detection circuit to selectively sense the cardiac signal of interest. The automatic gain control enables the device 100 to sense low amplitude signal characteristics of atrial or ventricular fibrillation.

The outputs of the atrial and ventricular sensing circuits 244 and 246 are connected to the microcontroller 220 which, in turn, is able to trigger or inhibit the atrial and ventricular pulse generators 222 and 224 in a demand fashion in response to the absence or presence of cardiac activity in the appropriate chambers of the heart. The sensing circuits 244 and 246 receive control signals from the microcontroller 220 over signal lines 248 and 250 for purposes of controlling the gain, threshold, polarization charge removal circuitry (not shown), and the timing of any blocking circuitry (not shown) coupled to the inputs of the sensing circuits.

Cardiac signals are supplied to an analog-to-digital (ND) data acquisition system 252, which is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, and the right ventricular lead 108 through the switch 226 to sample cardiac signals across any pair of desired electrodes.

The data acquisition system 252 is coupled to the microcontroller 220, or other detection circuitry, to assist in detecting an evoked response from the heart 102 in response to an applied stimulus, which is otherwise known as detecting "capture". Capture occurs when an electrical stimulus applied to the heart is of sufficient energy to depolarize the cardiac tissue, thereby causing the heart muscle to contract. The microcontroller 220 detects a depolarization signal during a window following a stimulation pulse, the presence of which indicates that capture has occurred. The microcontroller 220 enables capture detection by triggering the ventricular pulse generator 224 to generate a stimulation pulse, starting a capture detection window using the timing control circuitry 232 within the microcontroller 220, and enabling the data acquisition system 252 via control signal 256 to sample the cardiac signal that falls in the capture detection window and, based on the amplitude, determines if capture has occurred.

Capture detection may occur on a beat-by-beat basis or on a sampled basis. A capture threshold search can desirably be performed once a day during at least the acute phase (e.g., the first 30 days) and less frequently thereafter. A capture threshold search would begin at a desired starting point (either a high energy level or the level at which capture is currently occurring) and decrease the energy level until capture is lost. The value at which capture is lost is known as the capture threshold. Thereafter, a safety margin is added to the capture threshold.

The microcontroller 220 is further coupled to a memory 260 by a suitable data/address bus 262. The programmable operating parameters used by the microcontroller 220 are stored in memory 260 and used to customize the operation of the device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 102 within each respective tier of therapy.

The operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 allows intracardiac electrograms and status information relating to the operation of the device 100 (as contained in the microcontroller 220 or memory 260) to be sent to the external device 254 through an established communication link 266.

The implantable cardiac device 100 can further include one or more physiologic sensors 270. Such sensors are commonly referred to as "rate-responsive" sensors because they are typically used to adjust pacing stimulation rates according to the exercise state of the patient. However, the physiological sensor 270 may further be used to detect changes in cardiac output, changes in the physiological condition of the heart, or diurnal changes in activity (e.g., detecting sleep and wake states). Accordingly, the microcontroller 220 responds by adjusting the various pacing parameters (such as rate, AV Delay, V-V Delay, etc.) at which the atrial and ventricular pulse generators 222 and 224 generate stimulation pulses. While shown as being included within the device 100, the physiologic sensor(s) 270 may also be external to the device 100, yet still be implanted within or carried by the patient. Examples of physiologic sensors that may be implemented in device 100 include sensors that, for example, sense respiration rate and/or minute ventilation, pH of blood, ventricular gradient, and so forth.

The implantable cardiac device 100 additionally includes a battery 276 that provides operating power to all of the components shown in FIG. 2. The battery 276 is capable of operating at low current drains for long periods of time (e.g., less than 10 μA), and is capable of providing high-current pulses (for capacitor charging) when the patient requires a shock pulse (e.g., in excess of 2 A, at voltages above 2 V, for periods of 10 seconds or more). The battery 276 also desirably has a predictable discharge characteristic so that elective replacement time can be detected. As one example, the device 100 employs lithium/silver vanadium oxide batteries.

The device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The device 100 further includes an impedance measuring circuit 278 that is enabled by the microcontroller 220 via a control signal 280. The impedance measuring circuit 278 is used for many things, including: lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves; and so forth. The impedance measuring circuit 278 is coupled to the switch 226 so that any desired electrode may be used.

In the case where the device 100 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 220 further controls a shocking circuit 282 by way of a control signal 284. The shocking circuit 282 generates shocking pulses of low (e.g., up to about 0.5 J), moderate (e.g., about 0.5 J to about 10 J), or high energy (e.g., about 11 J to about 40 J), as controlled by the microcontroller 220. Such shocking pulses are applied to the patient's heart 102 through at least two shocking electrodes selected, for example, from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of approx. 5-40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

The implantable cardiac device 100 described with respect to FIGS. 1 and 2 can be operated as a dual chamber pacing device that is capable of both detecting cardiac activity in multiple chambers of the heart and administering pacing therapy to multiple chambers of the heart. Of particular interest, the device 100 is configured to detect premature atrial contractions and apply responsive therapy. These capabilities with respect to PACs are described in more detail in the next section entitled "PAC Mode of Operation". Generally, the device 100 is capable of sensing at one site in the atria and delivering the PAC pacing response at one or more other sites. Possible implementations include sensing atrial activity in the distal coronary sinus and pacing in the high right atrium or sensing in the high right atrium and pacing in the distal coronary sinus.

PAC Mode of Operation

Figure 3A:
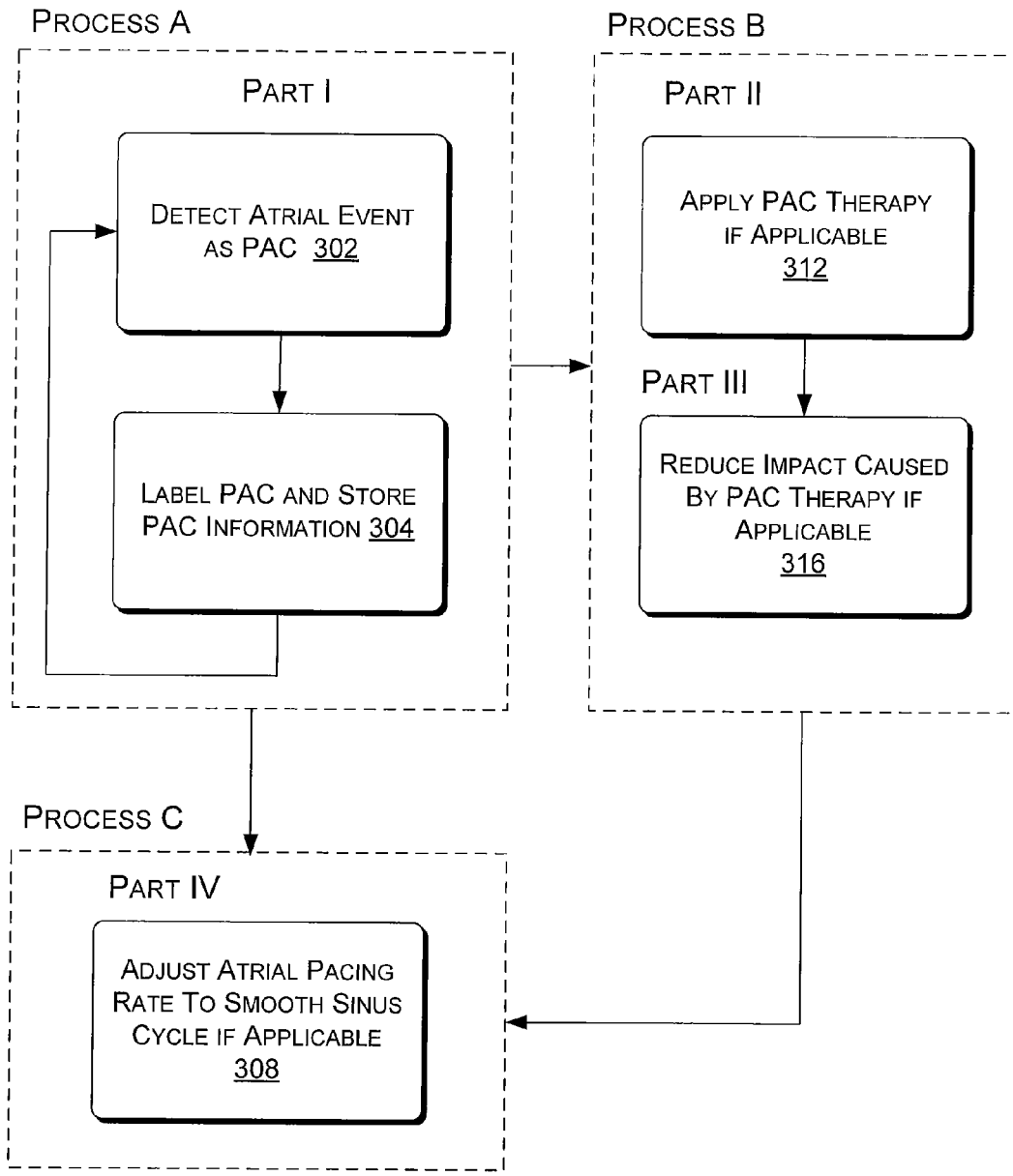
FIG. 3A is a flow diagram of a process for detecting premature atrial contractions (PACs) and administering responsive therapy.

FIG. 3A shows processes or methods 300 for handling premature atrial contractions (PACs). These processes 300 may be implemented in connection with any suitably configured device, although it will be described as being executed by the implantable cardiac device 100 of FIGS. 1 and 2 when operating in the PAC mode. In this flow diagram (as well as others that follow), the operations are summarized in individual "blocks". The operations may be performed in hardware and/or as machine-readable instructions (software or firmware) that can be executed by a processor, such as microcontroller 220.

Figure 3B:
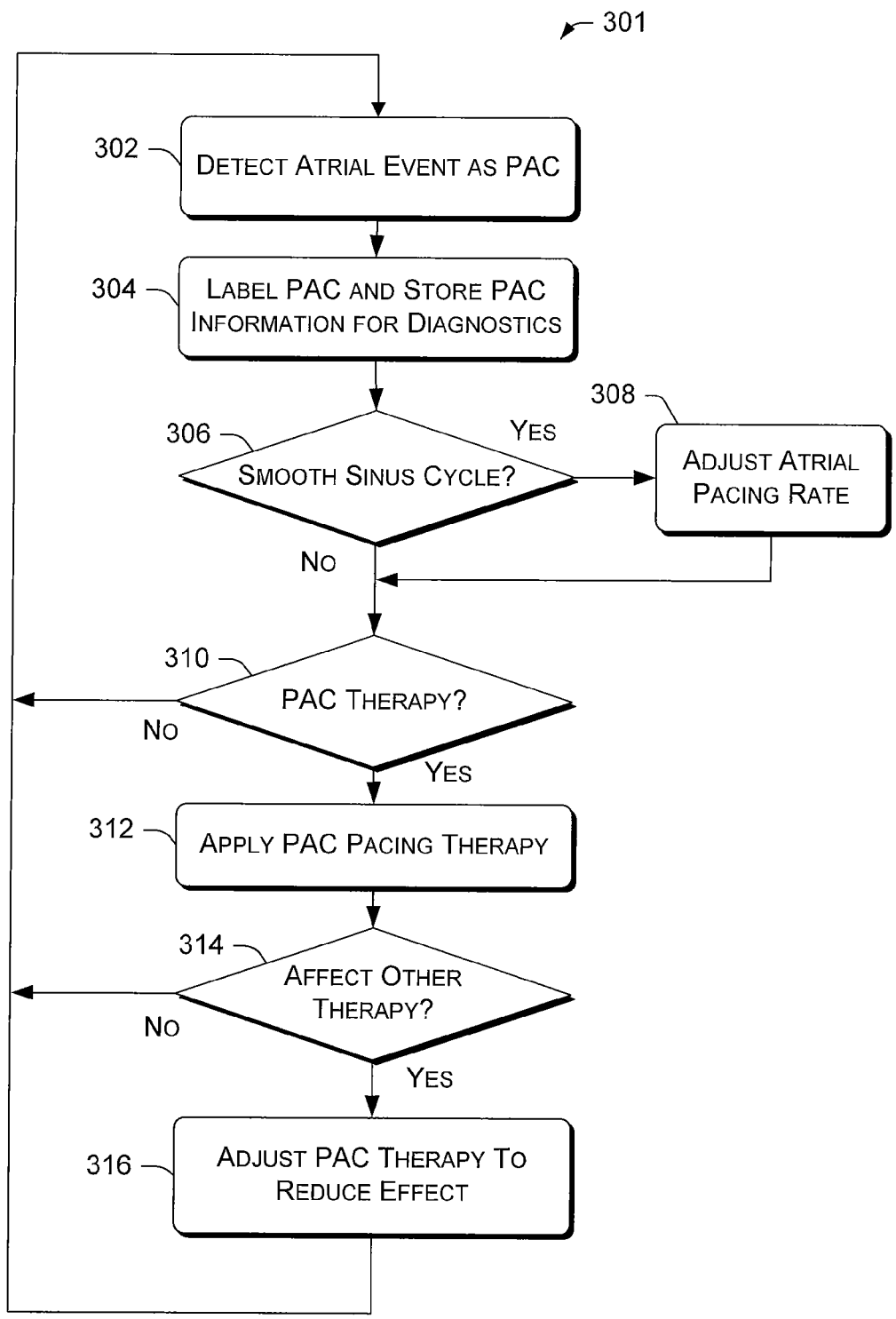
FIG. 3B is a flow diagram of a process for detecting premature atrial contractions (PACs) and administering responsive therapy.

FIGS. 3A and 3B show exemplary methods 300 and 301, respectively. The exemplary methods 300 of FIG. 3A includes four parts (Parts I-IV) organized as three processes (Processes A, B and C) where Part I is included Process A, Parts II and III are included in Process B and Part IV is included in Process C. The three processes may operate in a coordinated manner as indicated by various arrows. For example, Process A may invoke Process B and Processes A and B may invoke Process C and Process A may invoke Process C without invoking Process B.

Process A, as already mentioned, includes Part I, which is defined by two operation blocks 302, 304. A detection block 302 acts to detect an atrial event as being a PAC. For example, a device may identify atrial events originating from atrial ectopic foci as PACs, differentiate them from sinus events, and exclude atrial events detected during atrial flutter or atrial fibrillation. In one implementation, detection of an atrial event as a PAC occurs based on timing. Because PACs originate from locations in the atrium other than the sinus node, other ways to detect a PAC can be based on electrogram morphology, or based on direction of wavefront propagation.

A storage block 304 acts to label and store the PAC. Such information can be transmitted to an external device for review by a physician or other purposes. With the ability to discern PACs from sinus P-waves (i.e., atrial depolarization caused by native sinus node activity), an implantable cardiac device 100 can provide useful diagnostic information on PAC frequency and trends thereof. This information can be used to adjust drug therapies and to gain insight into the initiation of AF. The device might also use PAC detection to affect other pacing therapy. For example, detection of an acute rise in the frequency of PACs could trigger additional preventative measures The two blocks 302, 304 of Part I form a loop that may be implemented as appropriate. For example, a care provider may invoke such a loop based on any of a variety of factors. Such a loop may be implemented to gather diagnostic information or may be implemented to invoke appropriate therapy.

Where Process A is implemented to invoke appropriate therapy, therapy such as the therapy of Process B (e.g., Parts II and III) may be invoked. Part II of Process B is an operational block 312 that acts to apply PAC pacing therapy while Part III of Process B is an operational block 316 that acts to reduce impact of an applied PAC therapy (e.g., the PAC pacing therapy 312).

With respect to the PAC therapy block 312 (Part II), consider an example where a device is programmed to apply therapy in the form of an atrial extrastimulus to preempt initiation of a reentrant tachycardia. In this example, the atrial extrastimulus is timed to occur late enough after the PAC to ensure that the atrial capture of the extrastimulus results in atrial capture, but early enough that the resulting induced atrial depolarization does not conduct through the AV node to the ventricles in the case that the initiating PAC has already done so. If both of these criteria can be met, the extrastimulus is applied; otherwise, it is inhibited. Given that the device might also be administering pacing therapies for other cardiac conditions, there may be other factors that weigh in this decision.

Figure 10:
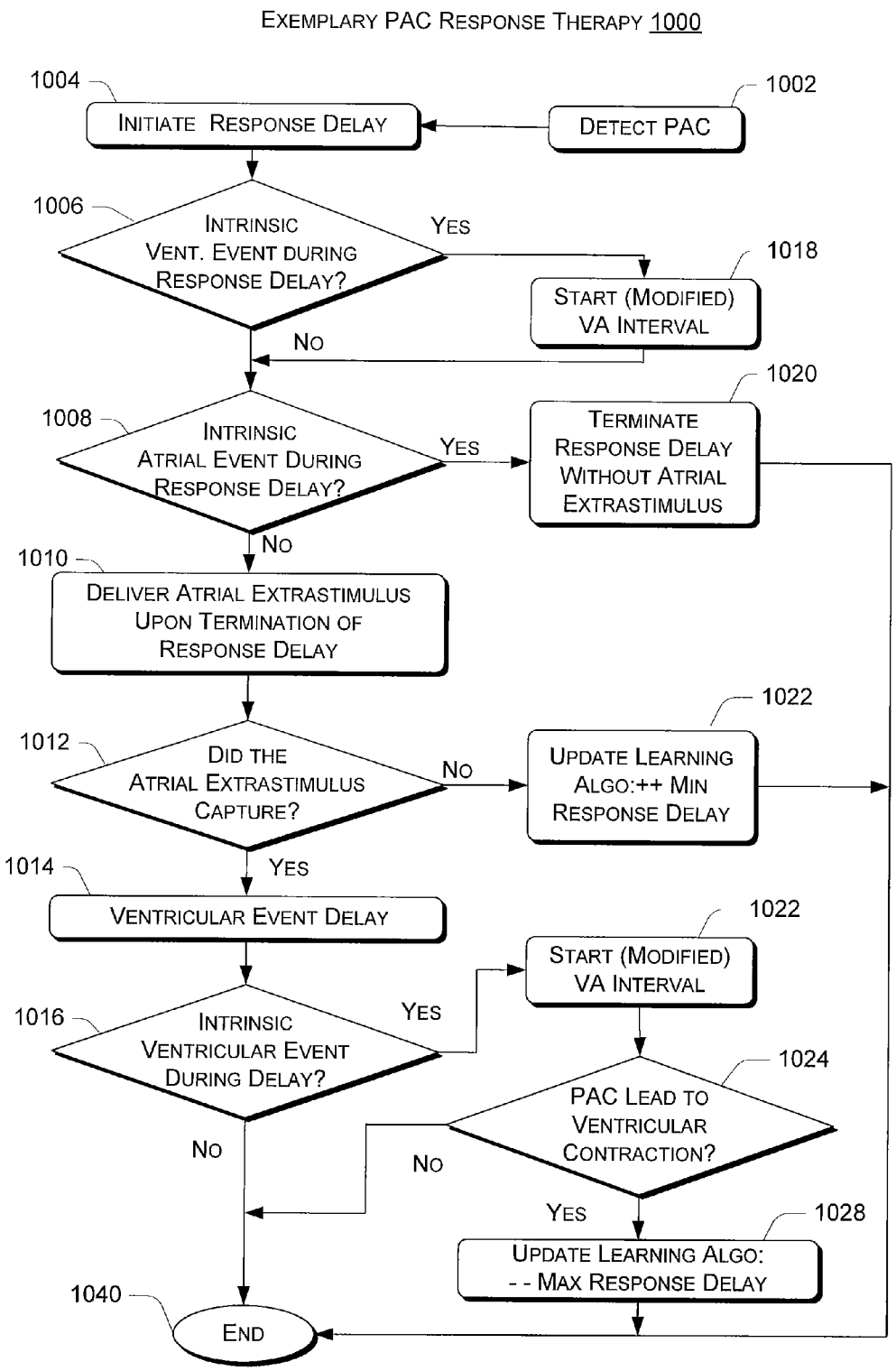
FIG. 10 shows exemplary processes for applying pacing therapy in response to detection of a PAC.

One or more reasons may exist that prevent call for or application of PAC therapy per the therapy block 312. For example, a PAC therapy module may be programmed on and a learning algorithm determines that at the given pacing rate, PAC therapy is inappropriate or not applicable. In another example, an intrinsic atrial event may occur during a response delay (see, e.g., block 1008 in FIG. 10) and detection thereof provide a signal to inhibit PAC therapy. In yet another example, (see, e.g., block 1006 in FIG. 10), which may be viewed as an alternative process that is not trying to learn about a maximum response, but inhibits PAC therapy upon detection of an R-wave. As shown in FIG. 10, detection of a PAC may occur during a response delay and, if a ventricular event is seen at step 1006, then the method terminates at block 1040. In such an example, the learning algorithm acts to avoid or prevent a second ventricular event. For example, the learning indicates that a PAC conducted and a response conducted; thus, use of a shorter AV delay may be called for to prevent conduction of an atrial event. If the delay is long, then such issues are generally a lesser concern; however, as sinus to PAC activity shortens, the PAC does not typically conduct and an atrial issue arises.

With respect to the impact block 316 (Part III), consider an example where a device avoids pacing a ventricle if too much time has elapsed since the last atrial depolarization in order to prevent initiating pacemaker-mediated tachycardia (PMT). Other response variations to minimize disruption are described below in more detail.

Process C may be invoked by processes such as Processes A or B. Part IV of Process C is an operation block 308 that acts to adjust atrial pacing rate to affect cardiac sinus cycle. Such a block may be implemented, for example, where adjustment of the atrial pacing rate occurs following an atrial extrastimulus in an effort to avoid a short-long cycle length sequence or to provide a smooth transition to the base rate over one or more pacing cycles.

While various operational blocks are included in various Parts or Processes, such blocks may be implemented in other manners, alone or in conjunction with other blocks, including blocks not shown in FIG. 3A.

FIG. 3B shows an exemplary method 301 that pertains to various operational blocks presented in the exemplary methods 300 of FIG. 3A. The exemplary method 301 typically occurs in conjunction with monitoring process that monitors cardiac activity. For example, an implantable device (e.g., the device 100) may sense cardiac activity on a substantially continuous basis while the exemplary method 301 acts to analyze such sensed activity to determine if a PAC has occurred.

The method 301 commences in the detection block 302 that detects an atrial event as a PAC, for example, based on IEGM data. The label and storage block 304 follows that acts to label the atrial event, for example, as the event is stored as IEGM data. Thus, subsequent presentation of the IEGM data may include a "PAC" label or other label indicative of detection of a PAC (e.g., on a display or printout).

Following the label and storage block 304, the method 301 enters a decision block 306 that decides whether to call for smoothing of the sinus cycle. If smoothing is desired, then the method 301 enters the adjustment block 308 that adjusts the atrial pacing rate in an effort to smooth the sinus cycle. According to the method 301, such an adjustment may act to smooth the sinus cycle in a manner whereby PACs do not occur. Thus, adjustment of an atrial pacing rate may be considered a first tier of a PAC therapy. However, as described herein, the term "PAC therapy" generally refers to higher tiers that explicitly aim to address PAC related issues through techniques other than simple adjustment to an atrial pacing rate alone.

The method 301 continues in another decision block 310 that decides whether to call for PAC therapy. For example, if PACs exist and an adjustment or adjustments to atrial pacing rate fail to remedy the situation (e.g., the adjustment block 308) or if the decision block 306 decides not to call for such smoothing via atrial pacing rate adjustment (e.g., the adjustment block 308), then the method 301 may call for PAC therapy that aims, at least in part, to eliminate PACs. If the decision block 310 decides to call for PAC therapy, then a therapy block 312 applies such PAC therapy. Otherwise, the method 301 returns to monitoring cardiac activity, optionally returning to the detection block 302, as appropriate.

In the instance that the method 301 applies PAC therapy per the therapy block 312, then yet another decision block 314 decides whether the applied PAC therapy is affecting or has affected other therapy or therapies. For example, a pacing therapy may be affected by implementation of the PAC therapy per the therapy block 312. If the decision block 314 decides that some therapy is being affected or has been affected, then the method 301 enters an adjustment block 316 whereby an adjustment occurs to the applied PAC therapy to reduce or eliminate adverse effects. As already mentioned, the method 301 may continue to monitor cardiac activity throughout, noting that various blocks cause the method 301 to return to the detection block 302 when appropriate, as based on sensed cardiac activity.

Various blocks of the exemplary methods 300, 301 of FIGS. 3A and 3B are described in more detail below. Also, various features of block 302 may be understood with reference to FIGS. 4-8 and 10; various features of block 304 with reference to FIG. 10; various features of block 308 with reference to FIGS. 19-21 (AV block, FIGS. 11 and 13; AV conduction, FIGS. 15 and 16); various features of block 312 with reference to FIGS. 9 and 10; and various features of block 316 with reference to FIGS. 11-22. Such features as described in these latter figures may be optional.

Part I: PAC Detection

As represented by operational block 302 in FIG. 3A, one task in treating a patient with premature atrial contractions is to appropriately detect PACs, which may include classifying certain atrial events as PACs. For example, such an operation may involve detecting an atrial event as originating from an atrial ectopic foci, differentiating it from sinus events, and excluding other atrial events detected during atrial flutter or fibrillation. In such an implementation, PAC detection and classification may be based on timing.

Timing-based PAC detection is based the assumption that, when a patient's heart is beating normally, any rate change of atrial events originating at the sinus node occurs gradually over several cycles. Accordingly, an abrupt change from one cycle to the next is probably caused by an abnormal event, such as a premature atrial contraction. An implantable cardiac device can monitor cardiac activity for any atrial events that occur within a specified time period after the previous paced or sensed atrial event.

Figure 4:
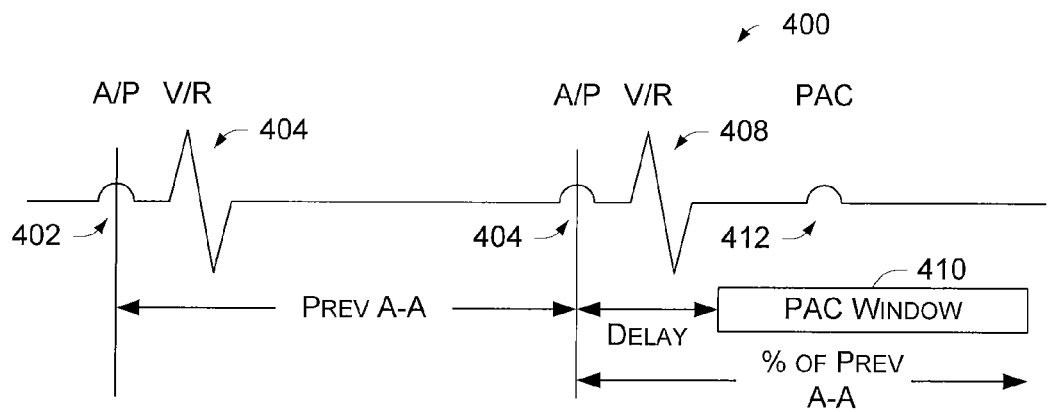
FIG. 4 shows a cardiac signal waveform representative of cardiac activity in a patient. The FIG. 4 waveform illustrates timing-based techniques for detecting a premature atrial contraction (PAC).

FIG. 4 shows an electrical signal waveform 400 indicative of cardiac activity sensed by the implantable cardiac device (e.g., intracardiac electrogram signals). In this diagram (as well as others that follow), a horizontal axis of time is implied. The cardiac waveform 400 includes an atrial event 402 in the form of a P-wave or an A-wave (e.g., atrial depolarization caused by an applied stimulus).

Throughout the description herein, "A/P" indicates an atrial depolarization caused by an applied atrial stimulus aimed at atrial pacing or by native sinus node activity. With respect to applied atrial stimuli aimed at atrial pacing, pacing rates are often determined by a fixed base rate or by any one of several algorithms which attempt to mimic a physiologically appropriate heart rate (e.g., rate hysteresis, rest rate, activity sensor, atrial overdrive, etc.). While the timing of a P-wave is usually based on when it is sensed or otherwise detected, the timing of an A-wave may be based on the delivery time of the applied atrial stimulus or when a corresponding atrial evoked response (e.g., atrial capture) is sensed or otherwise detected. In either instance, A-wave or P-wave, the resulting depolarization front propagates through the atria to the AV node, which, under normal conditions, introduces a natural delay that allows the atria to contract and fill the ventricles with blood. After the delay, the depolarization front propagates through the ventricles, causing them to contract and pump oxygenated blood to the body and deoxygenated blood to the lungs.

FIG. 4 also shows a ventricular event 404, which is caused by a depolarization conducted through the AV node, or by an applied ventricular stimulus. A conducted depolarization results in a QRS complex, which is commonly sensed or otherwise detected as, or referred to as, an "R-wave". However, an implantable pacing device may be programmed to pace the ventricle if the intrinsic PR or AR delay is too long (e.g., consider AV or other block).

An applied ventricular stimulus typically results in a ventricular evoked response (i.e., ventricular capture), which is referred to herein as a "V-wave". Combinations of R-waves and V-waves are possible. However, as described herein, and in the drawings, "V/R" indicates a V-wave or an R-wave. While the timing of an R-wave is usually based on when it is sensed or otherwise detected, the timing of a V-wave may be based on the delivery time of the applied ventricular stimulus or when a corresponding ventricular evoked response (e.g., ventricular capture) is sensed or otherwise detected.

After a period of time the cardiac cycle repeats, beginning with another A/P event 406 and followed by the ensuing V/R event 408. The time period between consecutive atrial events (A/P) is identified in the diagram as an A-A cycle.

For PAC detection, an implantable device (e.g., the device 100) may set a window of time 410 after an A/P event during which the device will listen for any other atrial event that might occur. This window 410 is thus referred to as the "PAC detection window", or simply "PAC window". If an atrial event occurs during the PAC window 410, as represented by PAC 412, the PAC detector 234 of the implantable cardiac device classifies the atrial event as a PAC.

In one implementation, the PAC window 410 is set to begin after a delay period triggered by the A/P event (again, which may be sensed or paced), which is illustrated in FIG. 4. The delay accounts for a physiologic atrial refractory period during which PACs cannot occur. Examples of possible delays have values that range from approximately 150 ms to approximately 250 ms, with 200 ms being a suitable delay. In another implementation, the delay may be set equal the AV (or PV) delay plus the post ventricular atrial blanking (PVAB) interval. In various dual chamber devices, the AV delay is the length of time between an atrial paced event and the delivery of a ventricular stimulus (i.e., ventricular output pulse). Similarly, the PV delay is the length of time between an atrial sensed event and the delivery of a ventricular stimulus. The PVAB is another parameter used in various dual chamber devices to identify a time period in which atrial sensed events are blanked from the atrial channel and are not used to compute the filtered atrial rate interval. The AV and PV delays and PVAB are parameters that can be programmed into the device or determined by another algorithm executing in the device to control other cardiac conditions.

The PAC window 410 may be set to terminate at some percentage of the duration of a pervious AA cycle that did not involve a PAC (i.e., where no PAC was detected). The PAC window 410 is sized such that subsequent A/P events are not identified as PACs. As one example, the PAC window 410 is programmable to end at approximately 35% to approximately 85% of the last non-PAC atrial cycle length (i.e., the time between the previous two A/P events where no intervening PAC was detected).

Figure 5:
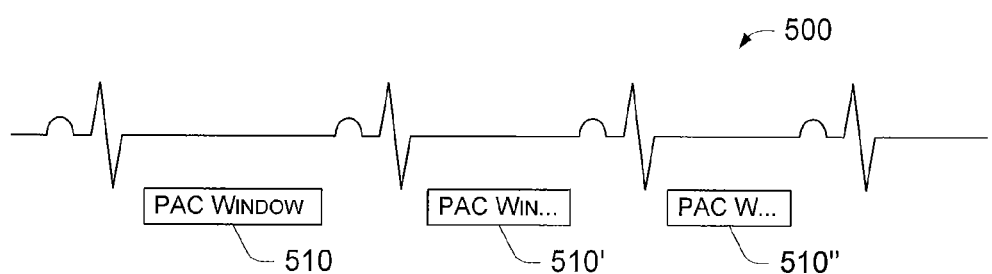
FIG. 5 shows a cardiac signal waveform to illustrate adaptation of a PAC detection window over several cardiac cycles.

FIG. 5 shows a signal waveform 500 having several cycles of varying length. In this waveform, changes in sinus rate occur gradually over several cycles. The PAC window 510, 510', 510" adjusts accordingly because its length is a percentage of the previous cycle length. In this example, the cycle is becoming shorter in time and the PAC window 510, 510', 510" is likewise becoming shorter. As a result, A/P events are not identified as PACs. A PAC is different from an A/P event in that the PAC causes a sudden shortening in the rate and hence would fall within the PAC window.

Figure 6:
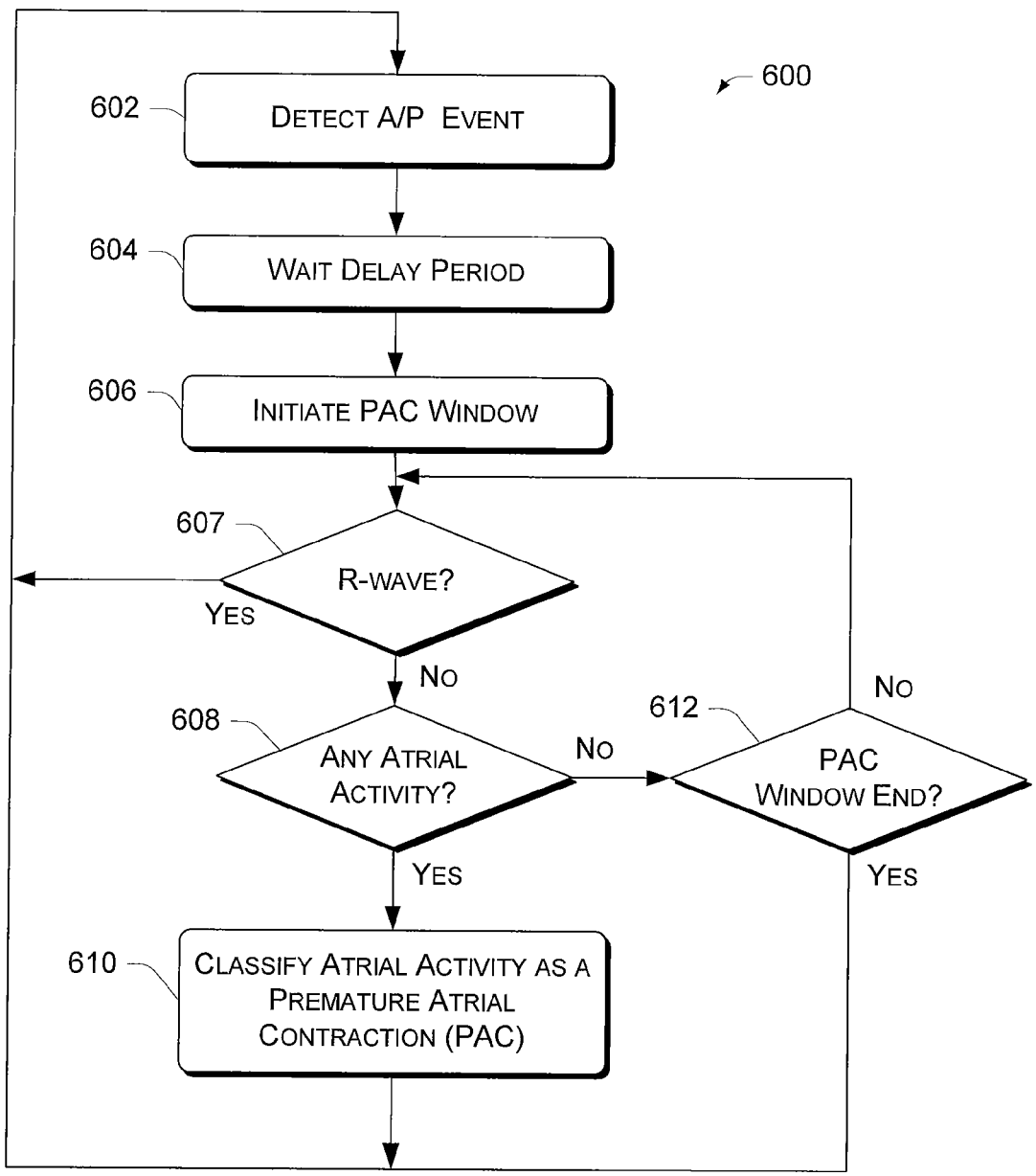
FIG. 6 shows a process for detecting and classifying a premature atrial contraction (PAC) using timing techniques.

FIG. 6 shows a process 600 for detecting and classifying a premature atrial contraction (PAC) using timing techniques. This process 600 is one possible implementation of the detection in operational block 302 illustrated in FIG. 3A. The process 600 can be implemented, for example, in the PAC detector 234 of the device 100.

At block 602, an exemplary device 100 detects an A/P event. In such detection, a P event may be further qualified as occurring outside of the atrial refractory period and, in some instances, this can be a requirement for further action (e.g., progressing to subsequent steps of the method 600). Upon the detecting of an A/P event, the PAC detector 234 initiates a delay (e.g., 200 ms) to account for atrial refractory period (block 604). In general, it is also expected that a paced or intrinsic ventricular event will occur during this delay. The delay may be set according to the requirement that it is greater than the AV delay or the PV delay, as appropriate. When the delay ends, the PAC detector 234 commences the PAC window (block 606) (e.g., the window 410, 510). Again, the PAC detector 234 may note delivery of an atrial pacing stimulus and may detect an A/P event, for example, in such a PAC window.

After initiation of the PAC window, a decision block 607 follows that decides if an R-wave occurred during the PAC window, irrespective of any ventricular refractory period. If the decision block 607 decides that an R-wave occurred, then the method 600 terminates the PAC window and returns to the detection block 602 or takes other appropriate action (e.g., monitoring or sensing for A/P events). Such action takes into consideration the fact that retrograde P-waves commonly follow PVCs. Thus, the process seeks to avoid detection or classification of retrograde P-waves as PVCs.

At block 608, the PAC detector 234 determines if any atrial activity has occurred within the PAC window (irrespective of the atrial refractory period). If the block 608 determines that atrial activity has occurred in the PAC window 410 (i.e., the "yes" branch from block 608), the PAC detector 234 classifies the atrial activity as indicative of a PAC (block 610). Thereafter, the method 600 may return to the detection block 602 or appropriate other action (e.g., monitoring or sensing for A/P events). Alternatively, if there is no atrial activity (i.e., the "no" branch from block 608), the PAC detector 234 determines whether the PAC window has expired (block 612). If not (i.e., the "no" branch from block 612), the PAC detector 234 continues to monitor ventricular and atrial activity; otherwise (i.e., the "yes" branch from block 612), the PAC detector 234 completes the cycle without classifying any PACs. The method 600 may return to the detection block 602 or take other appropriate action (e.g., monitoring or sensing for A/P events).

In addition to detecting a single PAC, an exemplary implantable cardiac device (e.g., the device 100) can be capable of detecting multiple consecutive PACs. For example, the device 100 can count consecutive PACs to identify "doublets" (i.e., two consecutive PACs), "triplets" (i.e., three consecutive PACs), or higher salvos of PACs. In this example, the PAC detector 234 maintains a counter 238 that is incremented (or decremented) with each PAC in a string of uninterrupted PACs.

Figure 7:
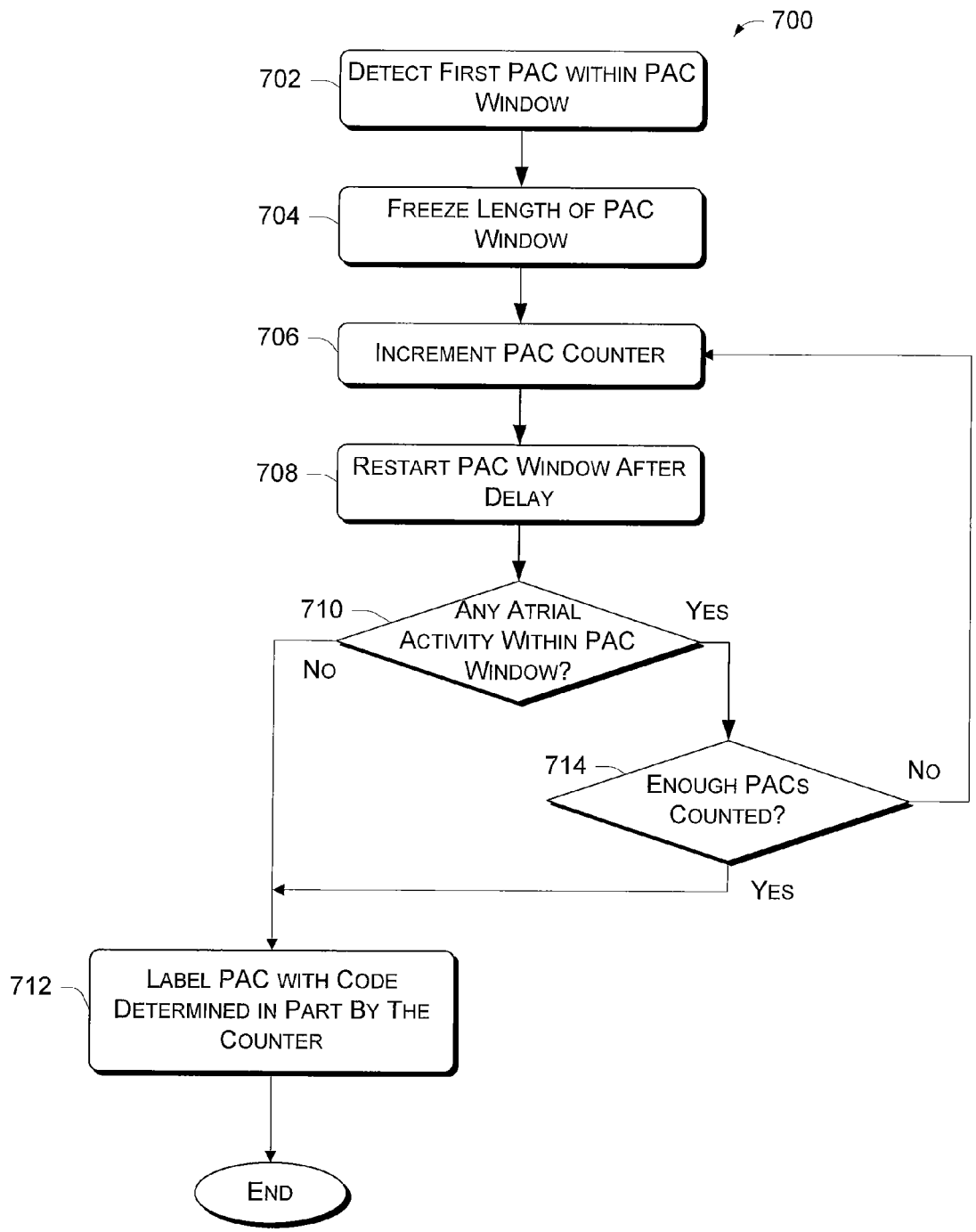
FIG. 7 shows a process for detecting a string of multiple consecutive premature atrial contractions (PACs) using timing techniques.

FIG. 7 shows a process 700 for detecting a string of consecutive premature atrial contractions using timing techniques. Such an exemplary process may be implemented using the device 100 and, in particular, a PAC module such as the PAC detector 234, which may be configured to implement such a process.

The exemplary process 700, implementing the PAC detector 234, at block 702, detects a first PAC. This operation can be performed according to the process 600 described above with respect to FIG. 6. Once the first PAC is detected, the exemplary device 100 fixes the length of the PAC window (e.g., the window 410, 510) to its current length (block 704). By freezing the PAC window and not allowing it to adjust to previous cycle lengths, the device does not adapt to an abnormally shortened cycle caused by the PAC. If the PAC window is allowed to shrink, a risk will exist of missing subsequent PACs that may not occur within the shortened window. Thus, in this example, the size of the PAC window remains constant for consecutive PACs until the window times out having acknowledged an absence of intrinsic atrial activity.

With detection of the first PAC, the PAC detector 234 increments a PAC counter (e.g., per the PAC module 234) to one (block 706). At block 708, the PAC detector 234 restarts the PAC window after the waiting delay (e.g., 200 ms). The PAC detector 234 then determines whether any atrial activity occurs during the PAC window (block 710). If atrial activity is sensed (i.e., the "yes" branch from block 710), the PAC detector 234 decides if enough consecutive PACs have been observed (block 714) and if not, increments the counter, such as from one to two (block 706), and restarts the PAC window after the waiting delay for the next cycle (block 708). This loop is repeated until enough PACs have been observed or until the PAC window times out with no intrinsic atrial activity.

Once the PAC window times out having acknowledged a lack of intrinsic atrial activity (i.e., the "no" branch from block 710), the PAC detector 234 characterizes the string of PACs as a single, doublet, triplet, or higher. More specifically, in this example, the PAC detector 234 labels the single PAC or the run of PACs with an event code "PAC#", where "#" is the count in the counter. In block 712, a single PAC may be identified by the event code PAC1, a doublet of PACs an event code of PAC2, and a triplet of PACs an event code of PAC3.

Also at block 712, the PAC events are logged in memory, such as memory 260 of the device 100. At a later time, diagnostic information about PAC events can be downloaded to an external device (e.g., the device 254) along with other diagnostic data for physician review. Information about PAC events may, for example, be stored as a count for each event code of the number of times that event code occurred. Similarly, a ratio or a percentage of PACs for a number of cycles (or time) may be used. PAC event codes may become part of the marker stream captured by an event-logging scheme or associated with a stored electrogram.

In the exemplary process 700, at block 714, after "enough" consecutive PACs (e.g. the fourth consecutive PAC) a unique event code (e.g. PAC4) is issued immediately. Four consecutive PACs can alternatively be classified as a short run of atrial tachycardia or atrial fibrillation. Therefore after enough consecutive PACs have been observed, further consecutive PACs are no longer identified as such until a PAC window times out having acknowledged a lack of intrinsic atrial activity.

Figure 8:
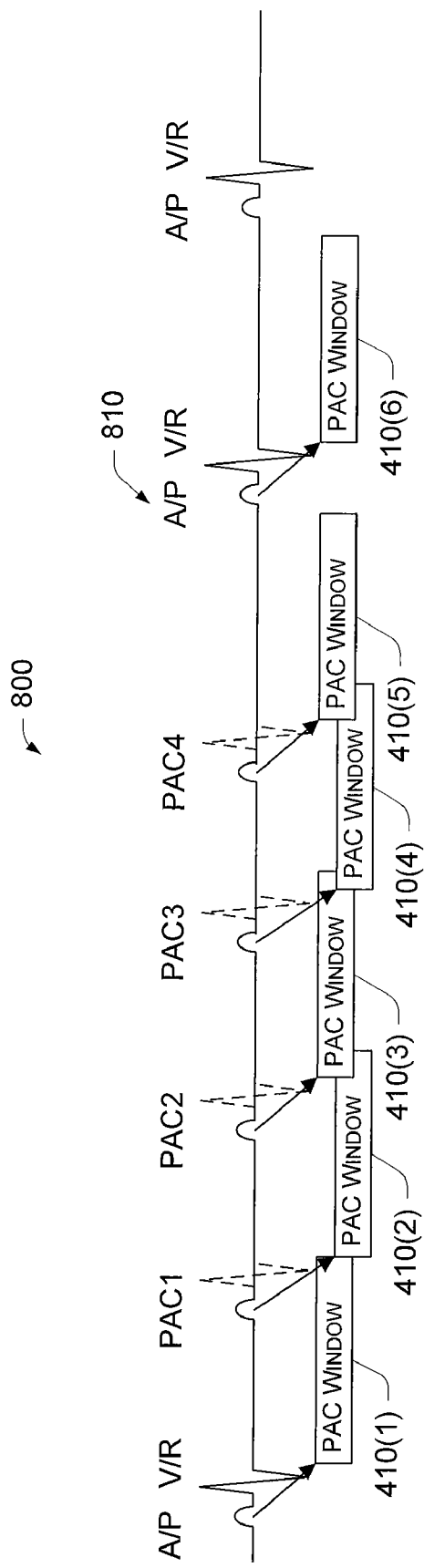
FIG. 8 shows a cardiac signal waveform to illustrate detection of multiple PACs.

FIG. 8 shows an exemplary waveform 800 having multiple successive PACs. A first PAC window 410(1) is triggered by an A/P event, as indicated by the arrow linking the A/P event to the window. The PAC window is started after a refractory delay (e.g., 200 ms). The next atrial event is detected as occurring within the first PAC window 410(1) and classified as a PAC.

Upon detecting and classifying the first PAC, an exemplary device (e.g., the device 100) freezes the size of the PAC window. That is, the size of PAC windows triggered by successive consecutive PACs remains the same as the size of the PAC window triggered by the first of the consecutive PACs until a PAC window times out with no intrinsic atrial activity within the window.

With each consecutive PAC, the device increments the counter and restarts the PAC window after the refractory delay. In FIG. 8, the next PAC window 410(2) is triggered by the first PAC (i.e., PAC1). The PAC window 410(2) has the same duration as the preceding PAC window 410(1). During the second PAC window 410(2), another atrial event is detected and classified as a PAC. This continues until a PAC window times out with no further atrial activity, as represented by subsequent PAC windows 410(3), 410(4), and 410(5).

When the PAC window finally times out, which inherently acknowledges a lack of intrinsic atrial activity during the PAC window, the implantable cardiac therapy device issues an event code for the run of PACs. Four consecutive PACs are illustrated as occurring within consecutive PAC windows 410(1), 410(2), 410(3), and 410(4), and this run of PACs is labeled PAC4 after the occurrence of the fourth PAC. When no event occurs during the final PAC window 410(5), a PAC counter is reset to zero, and the end time of the following PAC window 410(6) is calculated as a fraction of the time between the preceding two atrial events (i.e. PAC4 and A/P event 810) as described above.

The PAC detection process described above may be suspended if an implantable cardiac device detects atrial tachycardia or atrial fibrillation. Means by which cardiac devices detect atrial tachycardia or fibrillation are known in the art. When the episode of tachycardia or fibrillation ends, the PAC detection or PAC response process may be restarted, as appropriate.

It is noted that the cardiac device may be programmed to operate in a passive PAC detection mode where, for example, PACs are detected, classified and logged, but no responsive pacing is administered. In this example, other pacing operations are not affected by the passive PAC detection. However, the cardiac device may be operated in a response mode to administer responsive pacing therapy to detected PACs. This non-passive or responsive mode is described in the next section.

Part II: PAC Therapy

As depicted in block 312 in FIG. 3A (Part II), an exemplary implantable cardiac therapy device (e.g., the device 100) is programmable to selectively administer therapy in response to detection of a premature atrial contraction. Once an atrial event is detected as a PAC, the PAC module 234 can respond with appropriate PAC therapy.

In one implementation, the PAC module 234 applies a pulse in the form of an atrial extrastimulus (AX). To be effective, the timing of the extrastimulus is determined so as to ensure atrial capture. The atrial extrastimulus is issued some delay after detecting a single PAC or the first PAC in a run of PACs (e.g., PAC1 in FIG. 8). The atrial extrastimulus (AX) is intended to preempt additional PACs or initiation of a reentrant arrhythmia. Thus, the atrial extrastimulus (AX) is applied in response to detection of the first PAC, and not later PACs in a run of consecutive PACs. The atrial extrastimulus (AX) is timed to occur after the triggering PAC with a delay (to allow for passing of a physiologic refractory period caused by the PAC). This delay is chosen so that (i) that the extrastimulus results in atrial capture while (ii) the AV node, if it was depolarized by the PAC, is still refractory so that the depolarization wavefront initiated by the capturing AX pulse does not also conduct through the AV node to the ventricles. In cases where these conditions are not met, the device may elect to forego administration of the atrial extrastimulus. Of course, the latter condition (ii) is met where AV conduction is nonexistent or insufficient such that no or minimal risk exists for conduction of an atrial event.

Figure 9:
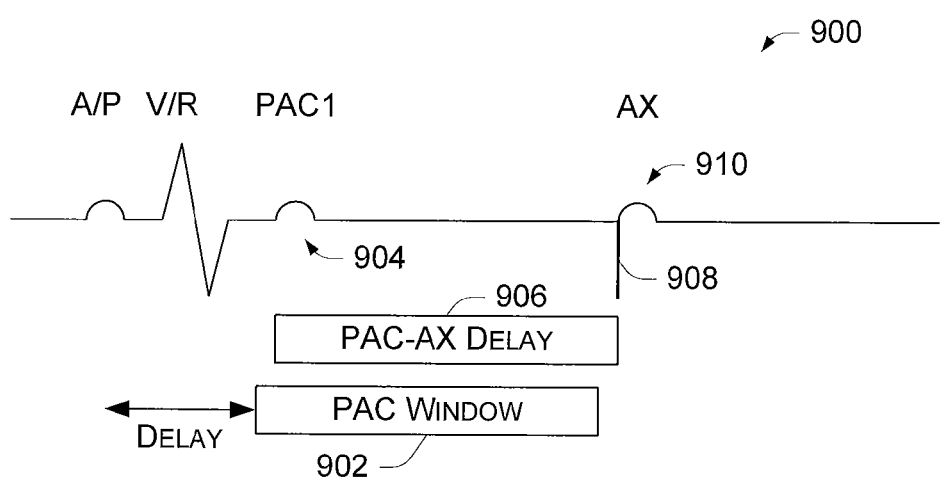
FIG. 9 shows a cardiac signal waveform to illustrate administration of a stimulation pulse in response to detection of a PAC.

FIG. 9 shows a signal waveform 900 to demonstrate PAC response therapy. The signal waveform 900 includes an A/P event followed by an R/V event. A PAC window 902 is set following a prescribed delay after the A/P event. When the device is operating in therapy mode, the device may employ the same timing-based PAC window used for gathering diagnostics on PACs (i.e., PAC window 410), as described above. Alternatively, the device may use a separate detection window that works in a same or similar manner but is programmable independently from the diagnostics PAC window.

During the PAC window 902, another atrial event 904 occurs and is classified as a premature atrial contraction. Upon detection, a delay 906 is triggered. Upon termination of the delay, an exemplary device (e.g., the device 100) administers pacing therapy in the form of an atrial extrastimulus (labeled AX) 908. The extrastimulus carries a charge of approximately T to 2T, where T is an atrial threshold level that may be determined by the device (e.g., Auto Capture) to ensure atrial capture. The atrial extrastimulus (AX) 908 induces an atrial depolarization, as represented by the waveform 910.

The delay 906 between the PAC 904 and the extrastimulus 908 is referred to as a "response delay" or "PAC-AX delay". The response delay 906 is sufficiently long to ensure that the atrial extrastimulus 908 occurs after the end of the post-PAC physiologic absolute refractory and relative refractory (vulnerable) periods of the atrium, thereby ensuring capture of the atrium when the extrastimulus is applied (again, given a sufficient stimulus energy). This condition is met in FIG. 9, where the atrial extrastimulus 908 results in atrial capture as indicated by the atrial event 910.

If AV conduction exists, and a PAC conducts through the AV node and triggers a ventricular contraction (not shown in FIG. 9), the response delay 906 is further intended to be short enough that the atrial extrastimulus does not also conduct through the AV node and trigger an additional ventricular contraction. This condition is also met in FIG. 9, because the stimulus-initiated atrial event 910 does not conduct as indicated by the absence of a subsequent R-wave. For purposes of illustration, an exemplary range of the response delay varies from approximately 200 ms to 400 ms.

In the case of AV conduction, if the response delay does not meet these conditions, the atrial extrastimulus may be inhibited. More specifically, if the response delay is such that the atrial extrastimulus would not result in atrial capture (e.g., would be applied to refractory tissue) and/or would conduct through the AV node (e.g., would be applied when the AV node is not refractory), the device foregoes application of the atrial extrastimulus. Of course, in scenarios where AV conduction does not exist or is insufficient, there is no or little risk that an atrial extrastimulus could conduct and result in a ventricular contraction.

Various exemplary methods and scenarios presented below are germane to patients having AV conduction and/or germane to patients having insufficient AV conduction. For example, FIG. 10, described below, shows an exemplary process 1000 for PAC response therapies for patients having AV nodal conduction capable of conducting atrial depolarization to the ventricles (e.g., intact AV nodal conduction).

The exemplary process 1000 aims to deliver atrial therapy in a manner that does not disturb ventricular rate. For example, an atrial extrastimulus should not result in a ventricular contraction if a preceding PAC has already resulted in a ventricular contraction. In the exemplary process 1000, an intrinsic ventricular event sensed during a response delay cancels delivery of an atrial extrastimulus, and thus eliminates the possibility that the exemplary process 1000 could induce a second ventricular contraction. While such a course of action may prevent delivery of one or more beneficial extrastimuli, it alleviates a need for a learning algorithm to concern itself with keeping the response delay short in order to avoid disturbing the ventricular rate. Of course, a learning algorithm may still be optionally employed to keep the response delay long so that the extrastimulus captures.

The exemplary process 1000 optionally implements a learning algorithm to keep the response delay short enough so that if the PAC causes a ventricular contraction, the atrial extrastimulus will not. Thus, the exemplary process 1000 can deliver an atrial extrastimulus even in cases where a PAC conducts.

For cases where AV conduction is nonexistent or insufficient, there is no or little risk that a PAC or an atrial extrastimulus could conduct and result in a ventricular contraction.

The exemplary process 1000 includes operations such as those of blocks 302, 304 and 312 of FIG. 3A (e.g., Parts I and II). The process 1000 may be implemented, for example, by the exemplary device 100 using the PAC module 234.

At block 1002, an atrial event is detected as a PAC, for example, per the exemplary detection process 600 of FIG. 6. At block 1004, a response delay (e.g., the delay 906) is initiated. The response delay is set to a suitable duration to help ensure that the atrial extrastimulus results in atrial capture, but while the AV node is still refractory to ensure that the atrial extrastimulus or tissue response thereto will not conduct through to the ventricles. The duration of the response delay may be programmed (e.g., 300 ms to 400 ms) or learned by a learning algorithm (discussed below in more detail).

A decision block 1006 decides whether an intrinsic ventricular event occurred during the response delay. In the case that the decision block 1006 decides that an intrinsic ventricular event occurred during the response delay, the process 1000 continues at block 1018, which starts a ventricular to atrial timing interval, referred to as a VA interval (e.g., a reset may occur for ventricular-based pacemaker timing). The VA interval may be calculated using a timing controller (e.g., the controller 232 of FIG. 2). Alternatively, the VA interval may be modified by a PAC module (e.g., the module 234 of FIG. 2). Various examples are described further below with reference to Part III, for example, to provide for a smooth rate transition back to the base pacing or sinus rate after the sudden rate increase caused by the PAC.

Whether the decision block 1006 commences a modified VA interval or not, the process 1000 continues in another decision block 1008. The decision block 1008 decides whether an intrinsic atrial event occurred during the response delay. If the decision block 1008 decides that such an event occurred, then the process 1000 continues in a termination block 1020 that terminates the response delay without calling for or delivering an atrial extrastimulus. After termination of the response delay, the process ends 1040. If the decision block 1008 decides that an intrinsic atrial event did not occur during the response delay, then the process 1000 continues in a delivery block 1010 that calls for or otherwise causes delivery of an atrial extrastimulus upon termination of the response delay.

The delivery block 1010 may include action to ensure capture of the atrial extrastimulus, for example, setting stimulation energy to a level above a atrial capture current threshold (e.g., double the threshold). The exemplary process 1000 includes an optionally learning process that occurs if the atrial extrastimulus did not capture due to length of the response delay. An update learning block 1022 represents such a process whereby an algorithm (described further below) acts to increase the minimum response delay so that subsequent atrial extrastimuli may be provided a sufficiently long delay to help ensure capture. The process 1000 then proceeds to the end block 1040 and the process may repeat upon detection of a PAC per the detection block 1002.

In the case that the decision block 1012 decides that the atrial extrastimulus resulted in atrial capture, then the process 1000 commences a wait for a ventricular event delay per the delay block 1014. A ventricular event decision block 1016 follows the delay block 1014 that decides whether an intrinsic ventricular event occurred during the delay period. If the decision block 1016 decides that an intrinsic ventricular event did not occur during the delay period, then the process 1000 continues to the end block 1040; however, if the decision block 1016 decides that such an event did occur, then a start block 1022 starts a VA interval (see, e.g., the aforementioned VA interval).

After the VA interval start block 1022, the process 1000 continues at a decision block 1024 that decides if the detected PAC lead to a ventricular contraction. If the decision block 1016 decides the PAC did not produce a ventricular contraction, then the process 1000 continues to the end block 1040. However, if the PAC did produce a ventricular contraction, then the process 1000 continues in a learning block 1028. The learning block 1028 instructs the learning algorithm (described further below) to decrease the maximum response delay, so that subsequent atrial extrastimuli may not trigger a second ventricular contraction (i.e., wherein the first contraction is likely due to the PAC). The process then terminates in the end block 1040.

It is noted that an exemplary device capable of implementing the exemplary process 1000 may utilize one or more existing techniques for sensing or detecting atrial capture, refractoriness of the AV node, ventricular events, etc. For example, implantable cardiac devices produced by St. Jude Medical Corporation implement the AutoCapture™ pacing system, which can sense or detect atrial capture. This information is optionally shared with the PAC therapy unit 234 for purposes of making the decisions of various decision blocks in the process 1000.

Scenarios relevant to the exemplary process 1000 of FIG. 10 are described below. For example, in one scenario, where some degree of AV block exists, there is no or little chance for a PAC or an atrial extrastimulus to conduct to the ventricles and cause a ventricular contraction. Various decisions in the exemplary process 1000 are unlikely to occur and a PAC module may disable or otherwise not implement various branches based on such decisions.

Figure 18:
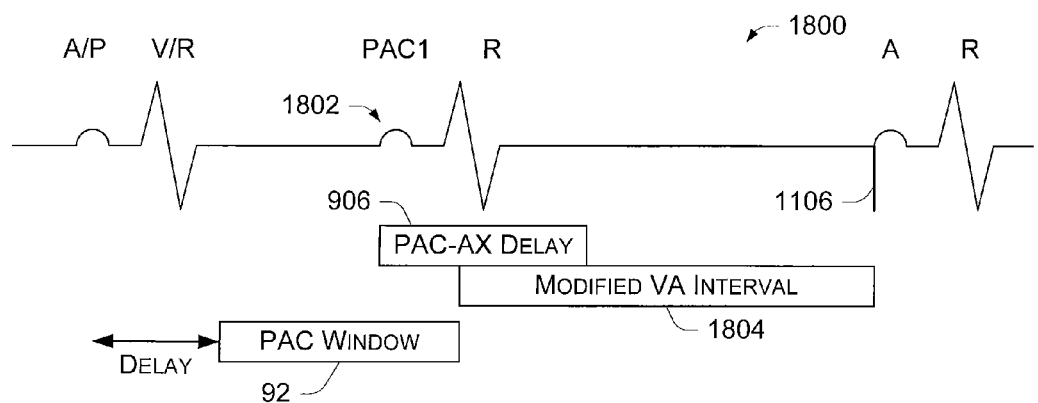
FIG. 18 shows a cardiac signal waveform that illustrates an alternative response for a patient exhibiting AV conduction, in which the scheduled atrial extrastimulus is cancelled in the event that the device senses an R-wave during a response delay occurring prior to administration of the atrial extrastimulus.

In various other scenarios, AV conduction exists and a delivered extrastimulus can result in a ventricular contraction whereas a detected PAC may not cause a ventricular contraction. Another AV conduction scenario, shown in FIG. 18, depicts how the exemplary process 1000 of FIG. 10 may apply where a PAC conducts. In this scenario, an R-wave triggered by the PAC is detected during the Response Delay, and the decision is taken at 1006 to start the VA interval at block 1018 and to optionally terminate the Response Delay without delivering an extrastimulus per the decision block 1008 and termination block 1020. The scenario of FIG. 18, also illustrates use of a modified VA interval (see, e.g., start block 1018), which is discussed in more detail below.

Various scenarios pertain to at least some degree of AV conduction (see, e.g., FIGS. 16 and 22), which have a ventricular contraction (e.g., an R-wave) that occurs during a Response Delay together with delivery of an atrial extrastimulus.

While the scenarios of FIGS. 11-22 are discussed in more detail below (see, e.g., Part III), together with reference to AV conduction or lack thereof, exemplary derivations of response delay are first discussed to understand relationships between AV conduction state and response delay.

With respect to the aforementioned response delay (or PAC-AX delay), the duration can be calculated in various ways. For example, one approach relies on a programmable response delay. A physician may set the response delay to an appropriate time interval for a given patient. Another approach is to use a learning algorithm to determine the length of the response delay. In this case, the learning algorithm may be implemented as part of the PAC therapy unit 234.

The minimum appropriate response delay is dependant on the PAC coupling interval, because the atrial refractory period is related to the previous atrial cycle length. The PAC coupling interval is the time from an A/P event to a PAC, or in this context, to an event classified as a PAC. In the case of AV conduction, the AV nodal refractory period is expected to be related to the time between conducted impulses. In the case when a PAC conducts through the AV node to the ventricles, this is expected to be close to the coupling interval of the PAC. The maximum appropriate response delay is dependant on the AV nodal refractory period. Therefore, both the minimum and maximum limits on the response delay following any given PAC depend on the coupling interval of that PAC.

Additionally, the relationship between coupling intervals and refractory periods is expected to be different from patient to patient. It is also expected to vary for each individual patient with autonomic, catecholaminergic, and pharmacological influences. Therefore, the relationship between the response delay and the PAC coupling interval can be adapted to each patient, and continually re-adapted over time. This is the function of the learning algorithm for the response delay.

An exemplary learning algorithm implements two array variables in the memory of the implantable device (260 in FIG. 2). The arrays store values representing the estimated minimum and maximum appropriate values of response delay for each of a plurality of ranges of PAC coupling interval. Table 1 shows an exemplary set of 28 such PAC coupling interval ranges.

Table 1

Index and Intervals

| Index # | PAC Coupling Interval (ms) |
|---|---|
| Index 0 | 200-224 ms |
| Index 1 | 225-249 ms |
| Index 2 | 250-274 ms |
| . | . |
| . | . |
| . | . |
| Index 26 | 850-874 ms |
| Index 27 | ≧875 ms |

The array variables may have the exemplary names:
  Max Response Delay [n]
  Min Response Delay [n]

In the case of this example, n may equal 0 to 27 and thus associate each array element with a range of PAC coupling interval listed in Table 1.

The response delay learning algorithm may have the following constants associated with it:
  Response Delay Abs Min~approximately 200 ms
  Response Delay Abs Max~approximately 400 ms When the learning algorithm initializes, e.g. when the PAC Response feature is enabled by a physician, Max Response Delay[n] may be set equal to Response Delay Abs Max for all n (i.e. 0 through 27). Also, Min Response Delay[n] may be set equal to Response Delay Abs Min for all n. During operation of the learning algorithm, no element of Max Response Delay is allowed to be greater than Response Delay Abs Max, and no element of Min Response Delay is allowed to be less than Response Delay Abs Min.

According to this exemplary scheme, every time an atrial extrastimulus (AX) is issued, the device determines whether AX resulted in capture of the atrium, fusion and/or pseudofusion, or non-capture. This analysis can be performed, for example, using the beat-by-beat atrial AutoCapture algorithm available as part of the AutoCapture™ pacing system in devices manufactured by St. Jude Medical Corporation.

This analysis is represented by the blocks 1022 and 1028 of FIG. 10. If the atrial extrastimulus is classified as non-capture, the learning algorithm increases Min Response Delay[n] by some time amount (e.g., 8 ms), where n may correspond to an index number defined in Table 1, which further corresponds to the length of the previous PAC coupling interval. Increasing Min Response Delay[n] will provide more time for the atrium to recover from the next PAC that has a coupling interval falling in range n, thereby improving the chance for the next AX to achieve atrial capture. If Min Response Delay[n] exceeds the upper bound Response Delay Abs Max, the Min Response Delay[n] is set equal to Response Delay Abs Max.

In the presence of intrinsic AV nodal conduction, the learning algorithm can keep the Response Delay short enough so that AX occurs within the AV nodal refractory period, and therefore does not cause a second ventricular contraction if the PAC has already done so. Therefore, block 1016 decides if an R-wave occurs during the delay period following AX, which is initiated at block 1014 (e.g., a delay of approximately 200 ms). If so, block 1016 may decide if a flag is set, (i.e. the preceding PAC had also caused an R-wave). If so, the Max Response Delay[n] is decreased by a time increment (e.g., 8 ms), where n is the index number defined in Table 1 corresponding to the duration of the previous PAC coupling interval. Decreasing the Max Response Delay attempts to keep the next AX within the AV nodal refractory period to thereby prevent the AX from causing a ventricular contraction in the presence of intrinsic AV nodal conduction if the PAC has already done so. If Min Response Delay[n] is less than the lower bound Response Delay Abs Min, the Min Response Delay[n] is set equal to Response Delay Abs Min.

The data thus stored in Max Response Delay[n] and Min Response Delay[n] can be used at the time a PAC is classified first to determine if an AX is allowed, and if so, to determine a value of Response Delay. If Max Response Delay[n]<Min Response Delay[n], where n is the index corresponding to the range in Table 1 which includes the just-measured PAC coupling interval, then AX is disallowed. It is noted that for some or all values of n in any given patient, AX may be thus disallowed. This is the desired behavior, as this would indicate that for some or all PAC coupling intervals in this patient, no value of Response Delay exists which will cause AX to reliably capture the atrium while not causing undue disruption to the ventricular rate by causing a second ventricular contraction after a PAC has already done so.

If it is determined that AX is allowed, the value of Response Delay may be calculated immediately after an atrial event is classified as a PAC. This may be done using the values of Min Response Delay[n] and Max Response Delay[n], where n is again the index corresponding to the range into which the coupling interval of the previous PAC fell. A Response Delay may be calculated as follows:

Response Delay=(Max Response Delay[$n$]+Min Response Delay[$n$])/2.

As an alternative, the Response Delay may be set equal to Min Response Delay[n]. Another alternative may set the Response Delay equal to Max Response Delay[n]. Selection between these alternatives for calculation of Response Delay may be made by the user via a programmable parameter. Many other functions relating Response Delay to the learned values of Max Response Delay[n] and Min Response Delay [n] can also be envisioned.

It may be desirable to allow the learning algorithm to "forget" as well, so that disallowing of AX need not be permanent. This may be achieved by periodically increasing Max Response Delay[n] and decreasing Min Response Delay [n] for all n by a value representing some time amount, e.g. 8 ms. Alternatively, only the values of n for which AX is disallowed may be affected. The periodicity may be tied to the passage of time (e.g. every week). Alternatively, the periodicity may be tied to the occurrence of some number of events, e.g. every 100 PACs or every 50 AXs issued. In the first example, the frequency with which AXs are re-attempted for values of n for which they had been disallowed increases with the frequency of PACs. In the latter example, AX may still be disallowed for all n. However, as long as there is some value of n for which AX may still be issued, the algorithm will occasionally re-attempt AX for other n.

The values of Max Response Delay[n] and Min Response Delay[n] stored in the device may be presented on demand to the user via a programming system.

Part III: Impact Reduction of PAC Response Therapy

As illustrated as block 316 in FIG. 3A, an exemplary implantable cardiac device (e.g., the device 100) may be configured to reduce the impact of the PAC response therapy on other therapeutic functions. That is, administration of the atrial extrastimulus may, in some cases, affect other pacing functions being performed by an exemplary implantable cardiac device. In dual chamber mode, for example, the device is capable of sensing both chambers of the heart as well as applying atrial pacing pulses or ventricular pacing pulses. When an exemplary device is additionally operated in PAC mode, the timing of these other pacing pulses may be adjusted depending upon when the PAC and responsive extrastimulus occur. These response adjustments are intended to reduce the impact to other pacing functions caused by a PAC or by administration of the PAC pacing therapy.

To illustrate these adjustments, two general types of patient conditions are described below: AV block and AV conduction. AV block describes the condition where there is no electrical conduction through the AV node between the atrium and the ventricles. AV conduction is the condition where conduction does occur through the AV node.

Case 1: AV Block

One possible stimulation therapy that might be affected by the PAC-responsive extrastimulus occurs in patients with AV block, where there is no significant conduction through the AV node. Typically, when a patient experiences AV block, the cardiac device 100 is operated in dual chamber mode in which both atrial pacing and ventricular pacing are administered.

Figure 11:
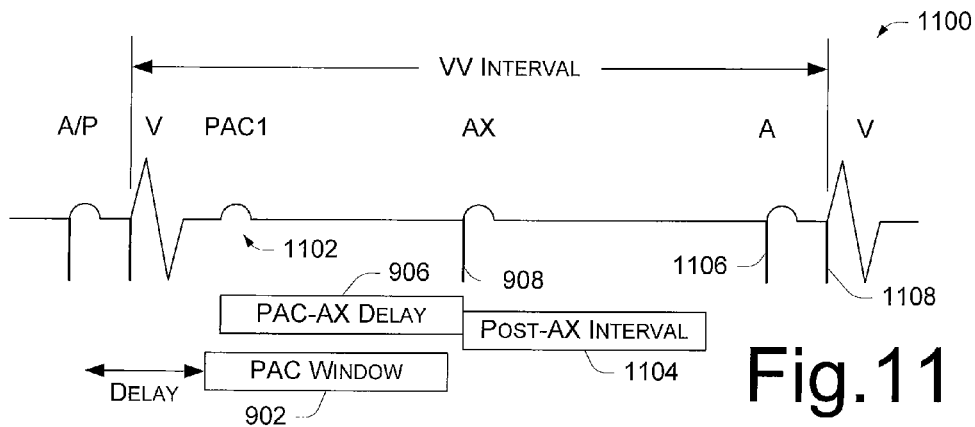
FIGS. 11-13 show cardiac signal waveforms representative of a patient with AV block, where
Figure 12:
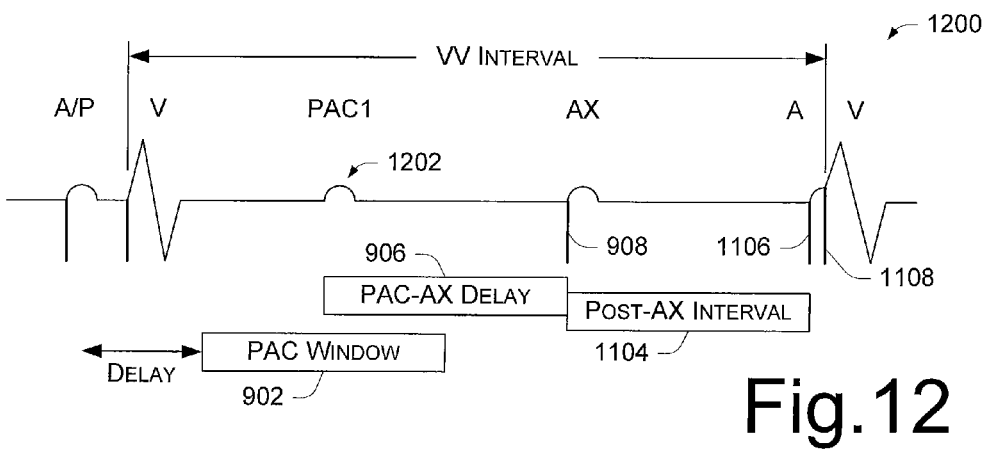
Figure 13:
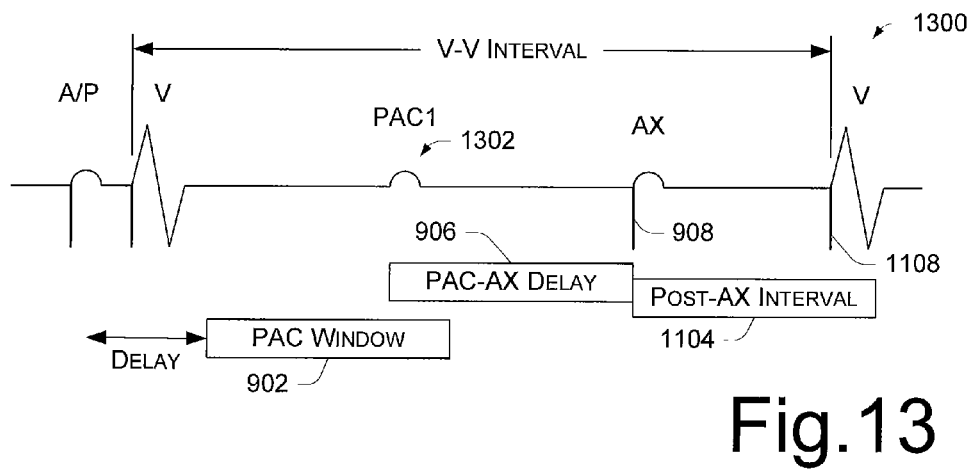

FIGS. 11-13 show cardiac signal waveforms representative of a patient with AV block (e.g., no intrinsic AV conduction). When operating additionally in the PAC mode and applying pacing therapy in the form of a PAC triggered atrial extrastimulus (AX) 908, the device 100 attempts to reduce any adverse effect on dual chamber pacing schemes for treating AV block by maintaining a constant ventricular interval and by maintaining AV synchrony to the extent possible in each cycle in which an atrial extrastimulus is delivered in response to a PAC. That is, the device 100 attempts to keep constant the interval between consecutive ventricular pacing pulses, which is referred to as the "V-V interval" or the "primary rate interval", for any cycle that contains a PAC. It is desirable to maintain a constant V-V interval to reduce the chance that a patient will experience symptoms caused by PAC therapy.

Depending upon the timing of the atrial extrastimulus 908 within the cycle and relative to the next scheduled ventricular pacing pulse, the device 100 determines whether and when to administer an atrial pacing pulse 1106 after the atrial extrastimulus 908 and before the ventricular pacing pulse 1106 scheduled at the end of the V-V interval. This pacing response is designed to maintain AV synchrony as much as possible while also allowing for a minimum interval between the atrial extrastimulus 908 and the atrial pacing pulse 1106. It is desirable to maintain AV synchrony to avoid causing symptoms and to maintain hemodynamic efficiency. Also assuring an atrial depolarization shortly before each ventricular contraction will reset the sinus node's natural timing and prevent a shortening of the subsequent cycle by a P-wave (tracking mode) or disassociation of the sinus and ventricular rates (non-tracking mode). It is desirable to have a minimum interval between the atrial extrastimulus and an atrial pacing pulse to prevent the atrial pacing pulse occurring during the atrial vulnerable period and thus possibly triggering an arrhythmia.

FIG. 11 shows a signal waveform 1100 with essentially the same timing of the PAC and response delay as shown in FIG. 9, where a PAC 1102 occurs early in a cardiac cycle and shortly after the paced ventricular stimulus and corresponding evoked response. Upon application of the atrial extrastimulus 908, the PAC therapy unit 234 initiates a post-AX interval 1104, which is the minimum delay from AX to the A-pulse scheduled to be delivered upon the end of the VA interval (i.e., the VV interval less the AV interval). The post-AX interval 1104 spans a sufficient time period that allows identification of any ventricular contraction resulting from AV conduction of the PAC. The post-AX interval may be programmable to various fixed time durations, which may be set according to the patient's cardiac profile. One example range of the post-AX interval is approximately 300-400 ms, with 350 ms being a suitable value. In FIG. 11, there is no AV conduction, as evidenced by the absence of an ensuing intrinsic R-waves following any of the atrial events.

To determine whether and when an atrial pacing pulse 1106 can be applied after the atrial extrastimulus 908 and before the ventricular pacing pulse 1108, the device determines when the post-AX interval 1104 will expire relative to the expiration of the VA interval and to the expiration of the VV interval. If the post-AX interval expires before the end of the VA interval as in FIG. 11, the device 100 applies the scheduled atrial pacing pulse 1106 at the end of the VA interval. In this example of an early PAC 1102, the device 100 is able to apply an atrial pacing pulse 1106 at its regularly scheduled time prior to the next scheduled ventricular pacing pulse 1108.

FIG. 12 shows a signal waveform 1200 where a PAC 1202 occurs later in the cycle in comparison to FIG. 11. When the atrial extrastimulus 908 is administered, the PAC therapy unit 234 begins the post-AX interval 1104. In this example, the post-AX interval 1104 ends after the scheduled atrial pacing pulse 1106 and before the scheduled ventricular pacing pulse 1108. The device 100 in this case delivers the atrial pacing pulse 1106 at the end of the post-AX interval 1104. Following the atrial pulse 1106, the ventricular pacing pulse 1108 is triggered to maintain the constant VV interval. In this case, the device shortens the AV delay in order to facilitate approximation of AV synchrony.

FIG. 13 shows a signal waveform 1300 where a PAC 1302 occurs even later in the cycle in comparison to FIGS. 11 and 12. In this case, the post-AX interval 1104 following the atrial extrastimulus 908 extends beyond the next scheduled ventricular pacing pulse 1108. Thus, there is no opportunity for the device 100 to administer the atrial pacing pulse after the post-AX interval but before the next scheduled ventricular pacing pulse. In this case, the device 100 foregoes the atrial pacing pulse, but applies the ventricular pacing pulse 1108 on schedule to maintain the constant VV interval. In this case, the atrial extrastimulus 908 occurring shortly in time before the ventricular pacing pulse 1108 approximates AV synchrony.

Figure 14:
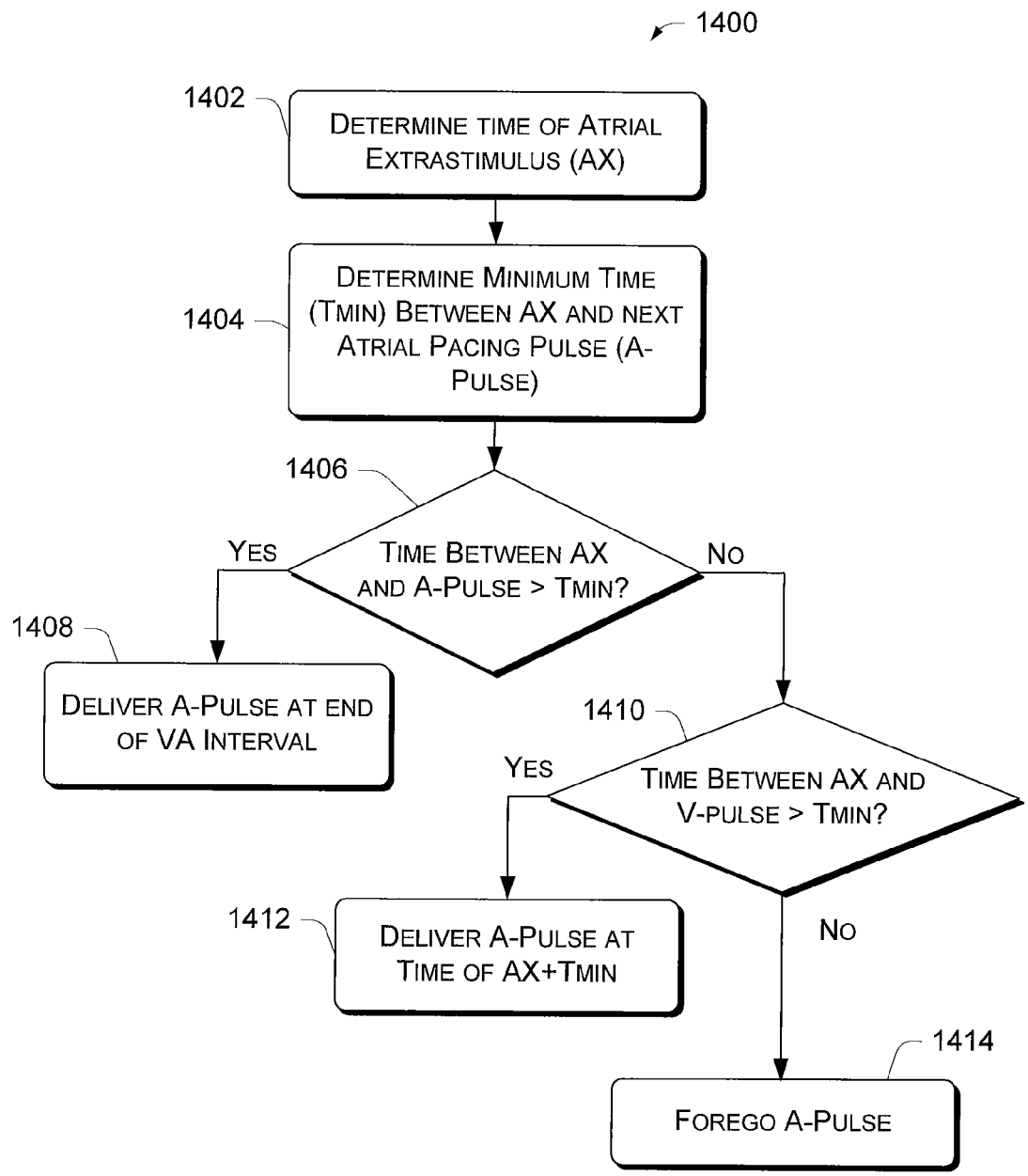
FIG. 14 shows a process for adjusting atrial pacing as a result of PAC detection and therapy when the implantable cardiac device is operating in dual chamber mode for a patient with AV block.

FIG. 14 shows a process 1400 for adjusting atrial pacing as a result of PAC detection and therapy when the device is operating in dual chamber mode for a patient with AV block. At block 1402, an exemplary device (e.g., the device 100) determines the time of an atrial extrastimulus (AX). A determination block 1404 determines the minimum time ($T_{Min}$) between the AX and the next atrial pacing pulse (A-pulse). A decision block 1406 follows whereby the difference between AX and A-pulse is compared with $T_{Min}$ to decide if the difference is greater than $T_{Min}$. If the difference is greater, then a delivery block 1408 calls for delivery of A-pulse at the end of the VA interval; whereas, if the difference is less than or equal to $T_{Min}$, then the process 1400 enters another decision block 1410.

The decision block 1410 decides if the difference between AX and V-pulse is greater than $T_{Min}$. If the difference is greater than $T_{Min}$, then a delivery block 1412 calls for delivery of A-pulse at a time of AX+$T_{Min}$; otherwise, an operational block 1414 causes the process 1400 to forego delivery of the A-pulse.

In this example, and other examples, the $T_{Min}$ may be determined through use of a lookup table, for example, adjusted or built by the learning algorithm. In such examples, instead of the PAC coupling interval determining an index however, it may be determined using the PAC-AX delay.

Case 2: AV Conduction

Figure 15:
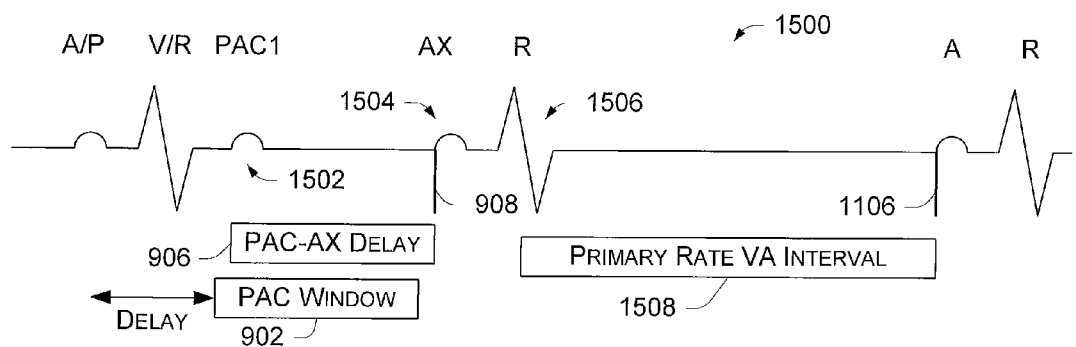
FIG. 15 shows a cardiac signal waveform in which a PAC occurs early in the cycle and the responsive atrial extrastimulus causes a ventricular contraction.
Figure 16:
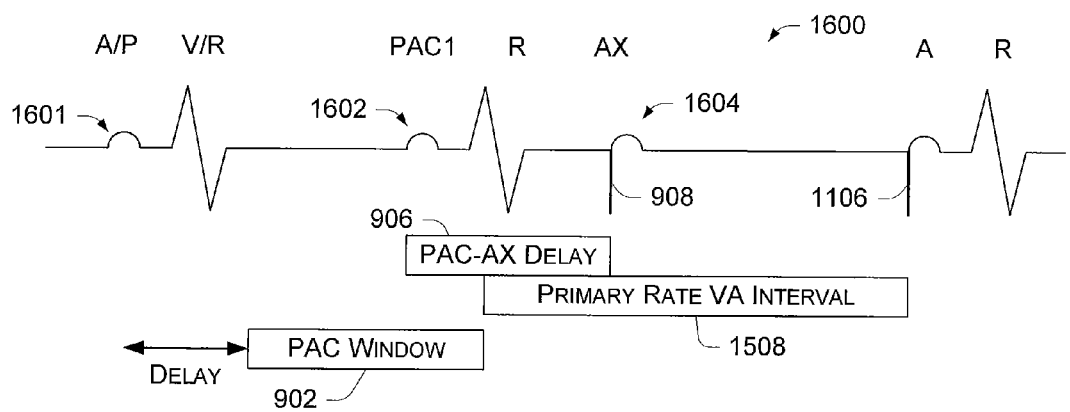
FIG. 16 shows a cardiac signal waveform in which a PAC occurs relatively late in the cycle and conducts through the AV node to the ventricles.

Another aspect of how therapy might be affected by the PAC-responsive extrastimulus occurs in patients where AV conduction is present. FIGS. 15 and 16 illustrate cardiac signal waveforms for a patient with normal AV conduction. In this case, the PAC or responsive atrial extrastimulus (AX) may conduct via the AV nodal pathway through to the ventricles, depending upon when the PAC or atrial extrastimulus occur. Therefore it may be impossible to prevent the atrial extrastimulus from disturbing the VV interval. For example, an exemplary device (e.g., the device 100) can respond by adjusting the timing of atrial pacing pulses to occur after a delay interval that commences upon detection of an R-wave induced by the PAC or atrial extrastimulus.

FIG. 15 shows a signal waveform 1500 in which a PAC 1502 occurs fairly early in the cycle and the responsive atrial extrastimulus AX causes a ventricular contraction 1506. With an early PAC, the AV node is still refractory and the PAC 1502 does not conduct through to the ventricles, as represented in waveform 1500 by the absence of any R-wave after the PAC 1502. The PAC therapy unit 234 administers an atrial extrastimulus 908 upon termination of the response delay 906. The atrial extrastimulus 908 captures the atrium or atria, as represented by the event 1504, and is subsequently conducted through AV node to the ventricles, resulting in an R-wave 1506 (R).

An exemplary implantable device can reset timing of the next scheduled atrial pacing pulse 1106 to occur upon termination of a primary rate VA interval 1508. Such a device can use the primary rate VA interval 1508 in other pacing modes to manage the duration between an R-wave (e.g., due to conducted atrial depolarization) and the next scheduled atrial pacing pulse 1106. The device 100 resets the primary rate VA interval 1508 upon detection of the R-wave caused by conduction of the atrial extrastimulus 908. Upon termination of the primary rate VA interval 1508, the device administers the next atrial pacing pulse 1106.

FIG. 16 shows a signal waveform 1600 in which a PAC 1602 occurs relatively late in the cycle and conducts through the AV node to the ventricles, as indicated by the ensuing R-wave. The PAC therapy unit 236 administers an atrial extrastimulus 908 upon termination of the response delay 906. The extrastimulus 908 captures the atrium, as indicated by the atrial depolarization event 1604. But, unlike FIG. 15, the AV node is refractory following termination of the PAC-AX delay 906 and hence, there is no conduction of the atrial extrastimulus 908 to the ventricles.

An exemplary implantable device (e.g., the device 100) can reset the primary rate VA interval 1508 upon detection of the native R-wave caused by the PAC 1602. Upon termination of the primary rate VA interval 1508, the device administers the next atrial pacing pulse 1106.

Figure 17:
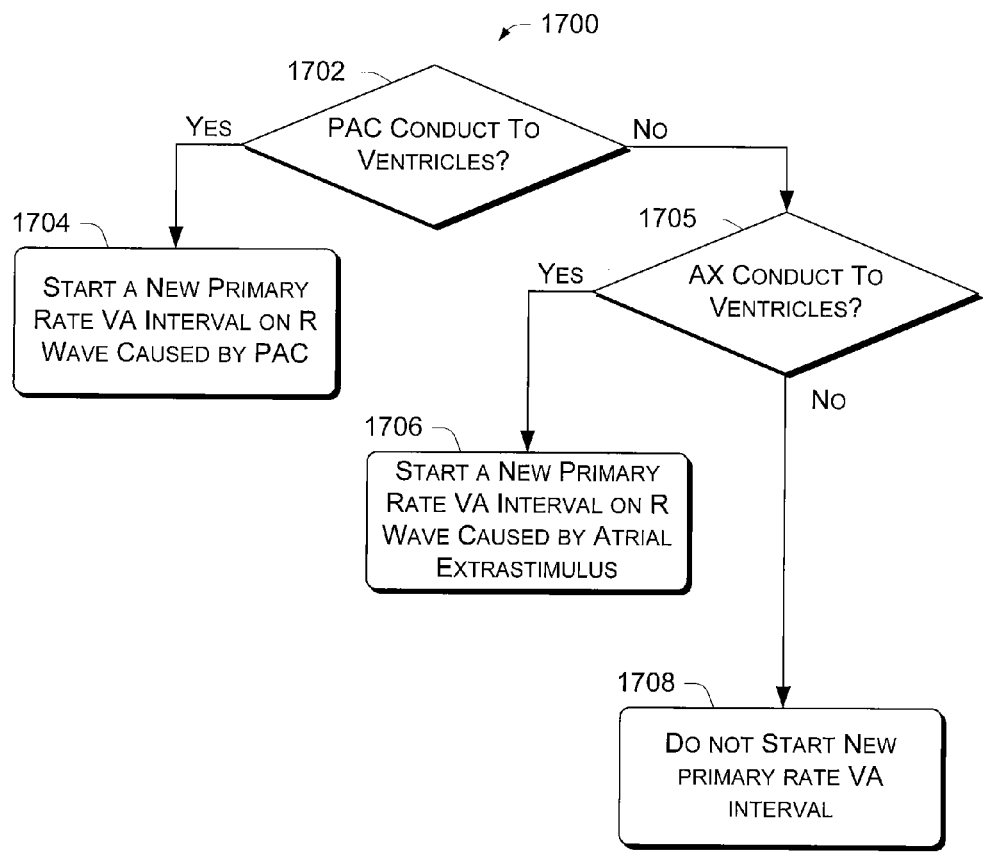
FIG. 17 shows a process for adjusting atrial pacing as a result of PAC detection and therapy when the patient exhibits normal AV conduction.

FIG. 17 shows a process 1700 for adjusting atrial pacing as a result of PAC detection and therapy when the patient exhibits normal AV conduction. At block 1702, an exemplary device decides whether a detected PAC conducts through the AV nodal pathway to the ventricles. In general, a PAC conducts when it occurs relatively late in the cycle after recovery, as represented in FIG. 15. When the PAC occurs relatively early, a delayed atrial extrastimulus, if applied, can conduct through to the ventricles, as represented in FIG. 16.

If AV conduction of the PAC occurs (i.e., the "yes" branch from block 1702), the device resets the primary rate VA interval to the ventricular R-wave induced by the PAC (block 1704). This is the case represented in FIG. 16. On the other hand, if the detected PAC does not conduct and thus does not cause a ventricular contraction (i.e., the "no" branch from block 1702), then the PAC is likely to have occurred early in the cycle while the AV node is still refractory. In this case, a decision block 1705 decides whether an AX delivered in response to the detected PAC conducts to the ventricles.

If the decision block 1705 decides that the AX conducted and caused a ventricular contraction, then a reset block 1706 resets the primary rate VA interval based on the R-wave or other indicia caused by the conducted AX. However, in the case that the AX does not conduct or does not otherwise cause a ventricular contraction (e.g., conduction via a non-AV nodal pathway), then a block 1708 prevents reset of the primary VA interval (e.g., retains current setting).

FIG. 18 shows the waveforms resulting from an alternative response for the AV conduction case, in which the scheduled atrial extrastimulus may be cancelled in the event that an exemplary device senses an R-wave during the PAC-AX delay. FIG. 18 shows a signal waveform 1800 with essentially the same timing waveform 1600 of FIG. 16. The PAC 1802 occurs late in the cycle and conducts through to the ventricles. In this example, the device is able to sense the subsequent R-wave caused by the PAC 1802 and, in response, the device cancels the atrial extrastimulus and initiates a modified VA interval 1804, which is shorter than the primary rate VA interval. Upon termination of the modified interval 1804, the device applies the next atrial pacing pulse 1106.

The modified interval 1804 may be derived in many ways. One approach is to set the modified interval equal to the primary rate VA interval less the AV delay. Another approach is to short the modified interval for purposes of atrial rate smoothing, as described below in the section titled "Atrial Pacing Rate Smoothing".

Part IV: Atrial Pacing Rate Smoothing

As illustrated as block 308 in FIG. 3A, an implantable cardiac device (e.g., the device 100) may optionally apply atrial rate smoothing techniques to avoid short-long cycle length sequences and/or provide a smooth transition to the base rate over one or more pacing cycles. Short-long sequences of atrial cycle length are potential triggers of atrial arrhythmias. These sequences can be created when a PAC with a short coupling interval is followed by an extended pause before the next atrial contraction, as may happen in nature when a single short-coupled PAC resets the sinus node. When a PAC occurs during the post-ventricular atrial refractory period, the normal response of the device in non-PAC mode is to ignore the PAC and provide an atrial stimulus one primary rate interval after the atrial event which preceded the PAC. This behavior can reduce the difference between the short interval preceding the PAC and the long interval following it.

When operating in PAC mode, the implantable cardiac device 100 can be configured to further reduce the difference between the short interval preceding the PAC (or atrial extra-stimulus) and the long interval which would otherwise follow it. The device introduces another, shorter interval, in comparison to the primary rate VA interval, that may be used to trigger the next atrial pacing pulse following a PAC or an atrial extrastimulus delivered in response to a PAC. The shortened interval is referred to as the "atrial rate stabilization interval".

One way to calculate the atrial rate stabilization interval (ARSI) is to split the difference between the PAC-AX delay 906 and the primary rate interval (PRI) where an atrial extrastimulus has been delivered. The calculation can be as follows:

$$ARSI = PAC\text{-}AX\ delay + (PRI - PAC\text{-}AX\ delay)/2$$

Figure 19:
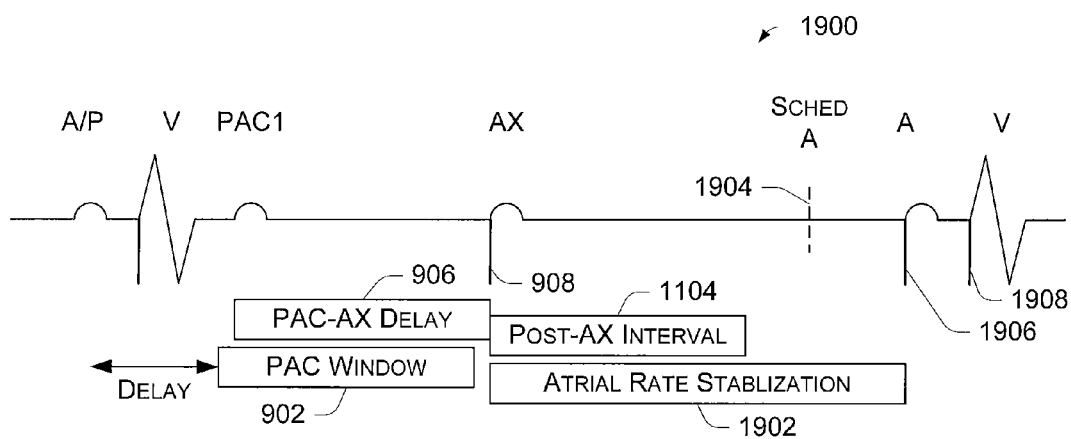
FIG. 19 shows a cardiac signal waveform with the same early PAC condition as shown in FIG. 11, but illustrates an alternate response in which the atrial pulse is timed by an atrial rate stabilization interval.
Figure 20:
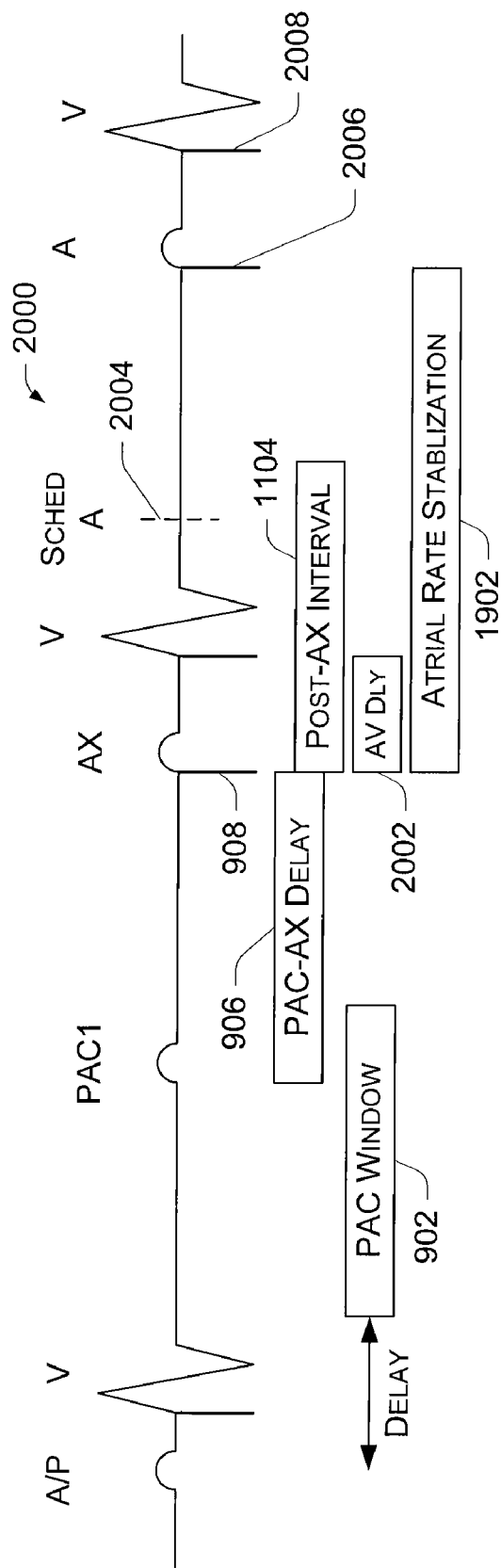
FIG. 20 shows a cardiac signal waveform that exhibits the same late PAC condition as shown in FIG. 13, but illustrates an alternate response in which the atrial pulse is timed by an atrial rate stabilization interval.
Figure 21:
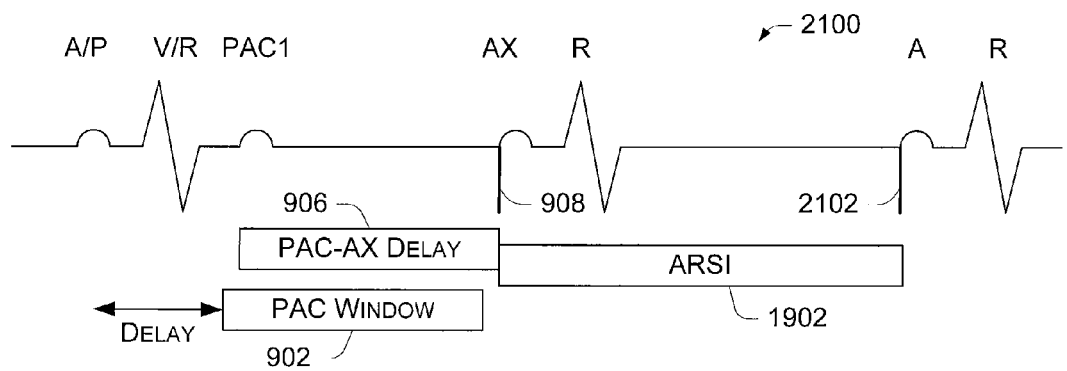
FIG. 21 shows a cardiac signal waveform with a similar pattern as that in FIG. 15, but illustrates an alternate response in which the atrial pulse is timed by an atrial rate stabilization interval.

FIGS. 19-21 illustrate use of the atrial rate stabilization interval to smooth the atrial pacing cycle. When using ARSI-timed pacing in PAC mode, the device does not attempt to maintain a constant V-V interval, as is done above in "Part III: Impact Reduction of PAC Pacing Therapy." When atrial rate stabilization is applied, the device allows for minimal disruption of ventricular rate in favor of a more regularized atrial rate.

Case 1: AV Block

FIG. 19 shows a signal waveform 1900 with the same early PAC condition as shown in FIG. 11, but illustrates an alternate response in which the atrial pulse is timed by the atrial rate stabilization interval. Here, the duration between the atrial extrastimulus 908 and the next scheduled atrial pacing pulse 1904 is greater than the post-AX interval 1104 (e.g., ~350 ms). An exemplary device (e.g., the device 100) can start the atrial rate stabilization interval 1902 upon application of the atrial extrastimulus 908. In the illustrated case, the atrial rate stabilization interval 1902 extends past the scheduled atrial pacing pulse 1904 to a delayed atrial pulse 1906 that is later in time. The delayed atrial pacing pulse 1906 is followed by a ventricular pacing pulse 1908, as appropriate for a patient with AV block. It is noted that an alternative way to calculate the atrial rate stabilization interval 1902 in this case is to calculate it as a normal VA interval, which is equal to the primary rate VA interval minus the AV delay.

FIG. 20 shows a signal waveform 2000 that exhibits the same late PAC condition as shown in FIG. 13, but illustrates an alternate response. Here, the duration between the atrial extrastimulus 908 and the next scheduled ventricular pacing pulse is less than the post-AX interval 1104. An exemplary device (e.g., the device 100) starts the AV delay 2002 and the atrial rate stabilization interval 1902 upon application of the atrial extrastimulus 908. Once again, the atrial rate stabilization interval 1902 extends past the scheduled atrial pacing pulse 2004 to a delayed atrial pulse 2006, which is then followed by a ventricular pacing pulse 2008.

Case 2: AV Conduction

Figure 22:
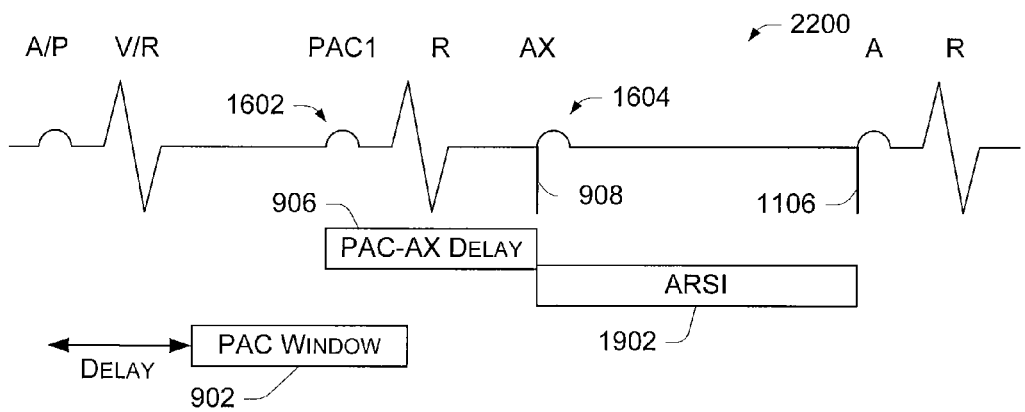
FIG. 22 shows a cardiac signal waveform with a similar pattern as that in FIG. 16, but illustrates an alternate response in which the atrial pulse is timed by an atrial rate stabilization interval.

In some cases, the premature atrial contraction or responsive atrial extrastimulus causes a disruption in ventricular rate because of native AV nodal conduction. In such cases, the device can apply atrial rate smoothing to reduce or minimize the disruption. FIGS. 21 and 22 show alternative responses to FIGS. 15 and 16, respectively, where the atrial pacing pulses are timed according to the atrial rate stabilization rather than the primary rate VA interval utilized in FIGS. 15 and 16.

FIG. 21 shows a signal waveform 2100 with a similar pattern as that in FIG. 15, where an atrial extrastimulus applied in response to an early PAC causes a ventricular contraction. When the extrastimulus 908 is applied following the response delay 906, an exemplary device (e.g., the device 100) initiates the atrial rate stabilization interval (ARSI) 1902 to time the next atrial pacing pulse 2102.

FIG. 22 shows a signal waveform 2200 with a similar pattern as that in FIG. 16, where a late PAC causes a ventricular contraction. After the response delay 906, the cardiac device 100 applies the atrial extrastimulus 908 and initiates the atrial rate stabilization interval 1902 to time the next atrial pacing pulse 2102.

It is further noted that the modified VA interval 1804 employed in FIG. 18 may be computed using the atrial rate stabilization interval. Recall that FIG. 18 shows an alternative response for the AV conduction case, in which the scheduled atrial extrastimulus is cancelled if an R-wave is sensed during the PAC-AX delay. In this alternative response, an exemplary device may apply a modified VA interval 1804, which is shorter than the primary rate VA interval. The modified VA interval 1804 can alternative be computed based on the ARSI, the PAC coupling interval (CI), and the primary rate interval, as follows:

ARSI=CI+(PRI−CI)/2

Modified AV Interval=ARSI−AV Delay

Figure 23:
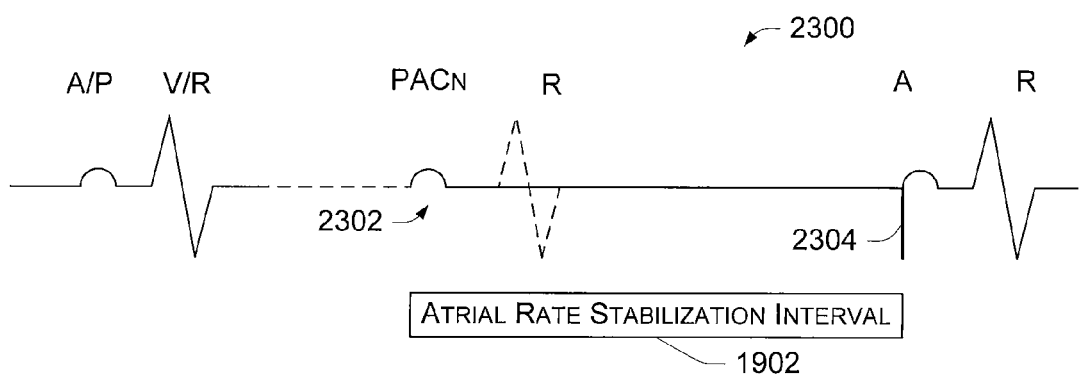
FIG. 23 shows a cardiac signal waveform in which the atrial rate stabilization interval is used to time an atrial pacing pulse following the last detected PAC in a string of consecutive PACs.

Because the atrial extrastimulus is only delivered after the first PAC, calculation of the atrial rate stabilization interval based on a PAC coupling interval is also applicable after the second or third PAC in a salvo of consecutive PACs. It applies to the interval following the last PAC of the salvo. The ARSI is maintained relative to the last PAC whether an R-wave occurs or not. FIG. 23 depicts this situation. A waveform 2300 has multiple consecutive PACs, with the last PAC (i.e., $PAC_N$) 2302 triggering the start of the atrial rate stabilization interval 1902. An atrial pacing pulse 2304 is applied upon termination of the interval 1902. The response of FIG. 23 to employ atrial rate smoothing based on the PAC coupling interval can also be generalized to apply to a single PAC where no atrial extrastimulus is delivered.

Exemplary State Machine

Figure 24:
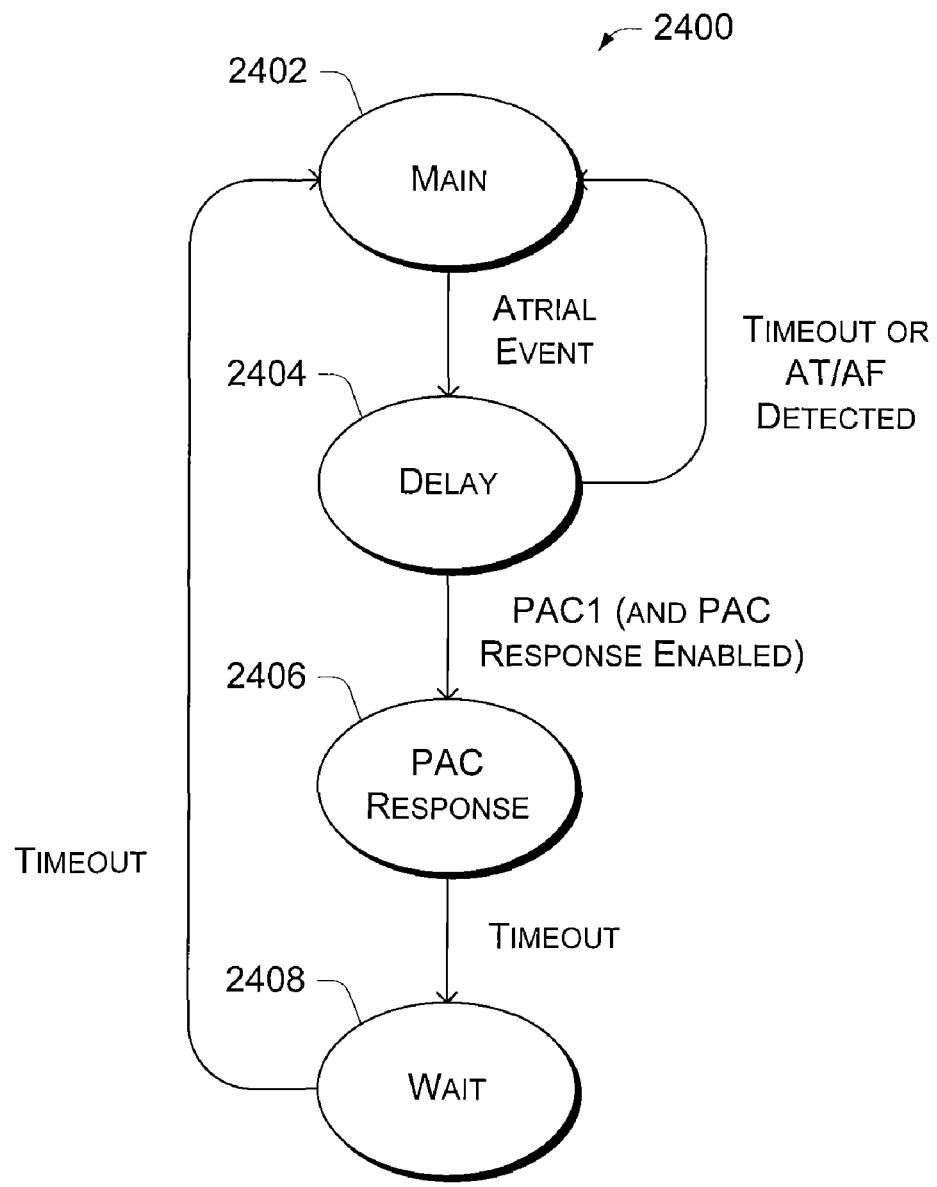
FIG. 24 shows an exemplary retrospective PAC detection/response state machine that may be implemented by the cardiac device to detect and respond to PACs.

FIG. 24 shows a diagram of an exemplary state machine 2400. Following initialization, the state machine enters the main state 2402. If atrial tachycardia and atrial fibrillation (AT/AF) are not present and a sensed atrial event occurs outside of the AV delay and outside of the post ventricular atrial blanking (PVAB), the state machine 2400 transitions to the delay state 2404.

In the state 2404, the machine 2400 delays for a prescribed time period, such as 200 ms. State 2404 determines if the sensed atrial event was a PAC. Depending on programming parameters, various actions may be taken if a PAC is detected. If a paced atrial event occurs while in the delay state 2404, there is no further processing and flow returns to the main state 2402 when the delay state times out. Transition may also be made to main state 2402 when the delay state 2404 times out.

If conditions for delivery of PAC response are met, the state machine 2400 transitions to the PAC response state 2406. Here, the machine 2400 may wait for a response delay equal to "Response Delay[n]", where n is the interval defined in Table 1. If AT/AF is present anytime during the PAC Response state (i.e., during Response Delay), the state machine transitions back to the main state 2402. Otherwise, when Response Delay[n] times out, the state machine 2400 may issue an atrial extrastimulus (AX), output an AX event code, and output the PAC event codes (e.g., PAC1, PAC2, PAC3, PAC4), as appropriate. The Response Delay[n] can be updated according to the response delay learning algorithm described above.

After the PAC Response state 2406, the state machine transitions to a wait state 2408, where the state machine waits for another period (e.g., 200 ms). If an R-wave occurs while in the wait state 2408, the Response Delay[n] is updated according to the response delay learning algorithm described above. The state machine transitions to the main state 2402 when the wait state times out.

Depending on programming, one action that may be taken is to Adjust Pacer State Machine for DDI on PAC as follows:

(1) Determine if there is enough time left after this PAC for the pacer state machine to deliver the scheduled atrial pacing stimulus at the end of the VA delay. There should be one post-AX interval (e.g., 350 ms) between this PAC and the scheduled atrial pacing stimulus. If there is one post-AX interval left before the atrial pacing stimulus, do no further processing and transition to the main state 2402 when the delay state 2404 times out.

(2) If there is not enough time, determine if there is at least one post-AX interval between the PAC and the scheduled ventricular pacing stimulus. If there is, lengthen the VA delay so that there will be one post-AX interval between this PAC and the A-pulse, shorten the AV delay by the same amount, do no further processing in the delay state 2404, and transition to the main state 2402 when this state times out.

(3) If there is not one post-AX interval between the PAC and the scheduled ventricular pacing stimulus, then inhibit the scheduled A-pulse completely. Do no further processing in this delay state and transition to the main state 2402 when the delay state times out.

Another action that may be taken in 2406 state upon detection of a PAC in 2404 may be to Adjust Pacer State Machine for Individual PAC Response as follows:

(1) Determine if there is enough time left after AX for the pacer state machine to deliver the scheduled atrial pacing stimulus at the end of the VA delay. There should be one post-AX interval (e.g., 350 ms) between the AX and the scheduled atrial pacing stimulus. If there is one post-AX interval before the atrial pacing stimulus, then do no further processing in this state and transition to the PAC Response state 2406.

(2) If there is not enough time, determine if there is at least one post-AX interval (e.g., 350 ms) between AX and the scheduled ventricular pacing stimulus. If there is, lengthen the VA delay so that there will be one post-AX interval between AX and the atrial pacing stimulus and shorten the AV delay by the same amount. Do no further processing in this state and transition to the PAC Response state 2406.

(3) If there is not at least one post-AX interval (e.g., 350 ms) between the AX and the scheduled ventricular pacing stimulus, then inhibit the scheduled atrial pacing stimulus completely. Determine if there is enough time to deliver AX before the scheduled ventricular pacing stimulus. If there is, then do no further processing in this state and transition to the PAC Response state 2406. If there is not, then do no further processing in this state and transition to the main state 2402 when this state times out.

CONCLUSION

Although various exemplary technologies have been described in language specific to structural features and/or methodological acts, it is to be understood that the subject matter defined in the appended claims is not necessarily limited to the specific features or acts described. Rather, the specific features and acts are disclosed as exemplary forms of implementing the claimed subject matter.

What is claimed is:

1. A method comprising:
   detecting a first atrial event of a sinus cycle;
   during the sinus cycle, initiating a detection window after detecting the first atrial event wherein the detection window comprises a duration less than a duration between consecutive sinus P-waves of a previous sinus cycle;

during the sinus cycle and during the detection window, detecting a second atrial event;

classifying the second atrial event as a premature atrial contraction of the sinus cycle;

in response to the detected second atrial event during the sinus cycle, reinitiating the detection window during the sinus cycle until one of the reinitiated detection windows times out with no additional atrial event being detected therein; and maintaining a count of consecutive premature atrial contractions.

2. The method of claim 1, wherein the detecting a first atrial event comprises detecting a native sinus P-wave.

3. The method of claim 1, wherein the initiating comprises starting the detection window after a preset delay following detection of the first atrial event.

4. The method of claim 1, wherein the detection window is of fixed duration.

5. The method of claim 1, wherein the detection window varies in duration for different cardiac cycles.

6. The method of claim 1, further comprising computing duration of the detection window as a percentage of a previous sinus cycle measured between consecutive sinus P-waves.

7. The method of claim 1, further comprising:

detecting and classifying one or more subsequent atrial events as premature atrial contractions until the detection window times out with no additional atrial event being detected.

8. An implantable cardiac device comprising:

sensing circuitry to receive signals indicative of atrial events caused by contraction of a patient's atrium; and a premature atrial contraction (PAC) detector operably coupled to the sensing circuitry, the PAC detector being configured to initiate a detection window after detection of an atrial event of a sinus cycle and to detect any subsequent atrial event that might occur during the initiated detection window, wherein the PAC detector classifies the atrial event detected during the detection window as a premature atrial contraction wherein the PAC detector reinitiates the detection window during the sinus cycle until one of the reinitiated detection windows times out with no additional atrial event being detected therein and wherein the PAC detector detects and counts multiple consecutive premature atrial contractions.

9. The implantable cardiac device of claim 8, wherein the PAC detector starts the detection window after a preset delay following detection of the atrial event.

10. The implantable cardiac device of claim 8, wherein the PAC detector derives the detection window as a percentage of a previous sinus cycle measured between consecutive sinus P-waves.

11. A method comprising:

(a) initiating a detection window in response to detecting an atrial event of a sinus cycle wherein the detection window comprises a duration less than a duration between consecutive sinus P-waves of a previous sinus cycle;

(b) detecting another atrial event that occurs during the detection window;

(c) classifying the other atrial event as a first premature atrial contraction;

(d) re-initiating the detection window after classification of the first premature atrial contraction;

(e) detecting a next atrial event that occurs during the detection window;

(f) classifying the next atrial event as a second premature atrial contraction; and further comprising repeating (d) through (f) to detect one or more additional premature atrial contractions until the detection window times out with no additional atrial event being detected and maintaining a count of consecutive premature atrial contractions.

12. The method of claim 11, further comprising, upon classification of the first premature atrial contraction, freezing the duration of the detection window.

13. The method of claim 11, further comprising labeling the first and second premature atrial contractions with labels that differentiate the first and second premature atrial contractions within a salvo of premature atrial contractions.

14. A method for detecting and classifying a salvo of consecutive premature atrial contractions (PACs), comprising:

detecting and classifying a first PAC during a detection window in a sinus cycle started in response to detecting a preceding atrial event in the sinus cycle;

restarting the detection window in the sinus cycle;

detecting and classifying one or more subsequent PACs until the detection window times out with no additional PAC being detected in the sinus cycle, wherein the detection window is restarted in response to detection of each atrial event in the sinus cycle; and maintaining a count of consecutive PACs in the sinus cycle.

15. The method of claim 14, wherein the detection window is started after a preset delay following detection and classification of each PAC.

16. The method of claim 14, wherein the detection window varies in duration for different sinus cycles until detection and classification of the first PAC, whereupon the detection window is fixed in duration until the detection window times out with no additional PAC being detected.

17. An implantable cardiac device comprising:

sensing circuitry to receive signals indicative of atrial events caused by contraction of a patient's atrium;

a premature atrial contraction (PAC) detector operably coupled to the sensing circuitry, the PAC detector being configured to detect and classify a sequence of premature atrial contractions by restarting a detection window after detection of each atrial event and classifying any atrial event detected during the detection window as a premature atrial contraction; and a counter to count a number of premature atrial contractions that occur in succession until one of the restarted detection windows times out with no additional atrial event being detected.

18. The implantable cardiac device of claim 17, wherein the PAC detector varies duration of the detection window for different sinus cycles until detection and classification of a first premature atrial contraction and then the PAC detector fixes the duration of the detection window until the detection window times out with no atrial event being detected.

19. The implantable cardiac device of claim 17, wherein the PAC detector labels the premature atrial contractions with labels to differentiate each premature atrial contraction within the sequence of premature atrial contractions.

20. A method comprising:

detecting a first atrial event;

initiating a detection window after detecting the first atrial event;

detecting a second atrial event during the detection window;

classifying the second atrial event as a premature atrial contraction;

reinitiating the detection window in response to detecting the second atrial event;

detecting and classifying one or more subsequent atrial events as premature atrial contractions until the detection window times out with no additional atrial event being detected, wherein the detection window is reinitiated in response to detection of each atrial event; and maintaining a count of consecutive premature atrial contractions.

* * * * *